(12) United States Patent
de la Huerga

(10) Patent No.: US 7,810,726 B2
(45) Date of Patent: Oct. 12, 2010

(54) METHOD AND SYSTEM FOR TRACKING AND VERIFYING MEDICATION

(76) Inventor: Carlos de la Huerga, 9190 N. Upper River Rd., Milwaukee, WI (US) 53217

( * ) Notice: Subject to any disclaimer, the term of this patent is extended or adjusted under 35 U.S.C. 154(b) by 0 days.

(21) Appl. No.: 11/961,441

(22) Filed: Dec. 20, 2007

(65) Prior Publication Data
US 2008/0093448 A1    Apr. 24, 2008

Related U.S. Application Data

(63) Continuation of application No. 11/220,426, filed on Sep. 7, 2005, now abandoned.

(60) Provisional application No. 60/607,551, filed on Sep. 7, 2004.

(51) Int. Cl.
*G06F 19/00* (2006.01)
*G06F 17/00* (2006.01)

(52) U.S. Cl. .................... 235/385; 235/375

(58) Field of Classification Search ........... 235/375, 235/380, 385, 462.01
See application file for complete search history.

(56) References Cited

U.S. PATENT DOCUMENTS

| | | | |
|---|---|---|---|
| 6,463,541 B2 | 10/2002 | Hu | |
| 6,996,543 B1 * | 2/2006 | Coppersmith et al. | 705/50 |
| 7,011,245 B1 | 3/2006 | Hu | |
| 7,175,081 B2 * | 2/2007 | Andreasson et al. | 235/385 |
| 7,387,249 B2 * | 6/2008 | Hudson et al. | 235/462.01 |
| 2002/0146146 A1 * | 10/2002 | Miolla et al. | 382/100 |
| 2003/0213844 A1 * | 11/2003 | Yoshida et al. | 235/383 |
| 2004/0205343 A1 | 10/2004 | Forth et al. | |
| 2005/0108044 A1 | 5/2005 | Koster | |

* cited by examiner

*Primary Examiner*—Thien M. Le
*Assistant Examiner*—April A Taylor
(74) *Attorney, Agent, or Firm*—Quarles & Brady LLP

(57) ABSTRACT

A method to verify a product produced by a manufacturer, the method comprising the steps of attaching a unique product code to a product prior to delivery to a retailer, storing the product code with product information in a first database linked to a verification system associated with the manufacturer, distributing the product to the retailer and selling the product from the retailer to a customer, the step of selling including the steps of using a first computer to obtain the unique product code from the product, providing the obtained product code to the verification system, comparing the obtained product code with the stored product code and when the obtained product code and the stored product code match, preparing a receipt including a verification code and providing the receipt to the customer.

38 Claims, 12 Drawing Sheets

200

| | Medication Information |
|---|---|
| 120 | Medication Name |
| 211 | Medication Manufacturer Information |
| 212 | Size/Concentration |
| 214 | Form/Shape |
| 215 | Initial Quantity of Medication in Container |
| 216 | Manufacturing Lot Number |
| 218 | Expiration Date |

| | Container Status Information |
|---|---|
| 222 | Ship Destination |
| 224 | Receiving/Dispensing Pharmacy Identification |
| 226 | Recall Status |
| 228 | New Contraindications |

| Retailer Identification Information |
|---|
| Identification Number<br>Password<br>Verification Code<br>Reader 260 Identification Code |

| Errors Retuned to Patient | |
|---|---|
| 630 | Bad Container Code, Medication Code, or Registration Code (not registered) |
| 632 | Dispensing Pharmacy not Registered |
| 634 | Dispensing Pharmacy Not Same as Receiving Pharmacy |
| 636 | Recall for Lot Number |
| 638 | Expiration Date |
| 228 | New Contraindications |
| 860 | Previously Sold to Different Customer |

| Patient Check Error | |
|---|---|
| 660 | Medication does not correspond to provided medication information (name, size, form, etc. errors) |
| 662 | Dispensing Pharmacy not the same as Pharmacy |

Fig. 15

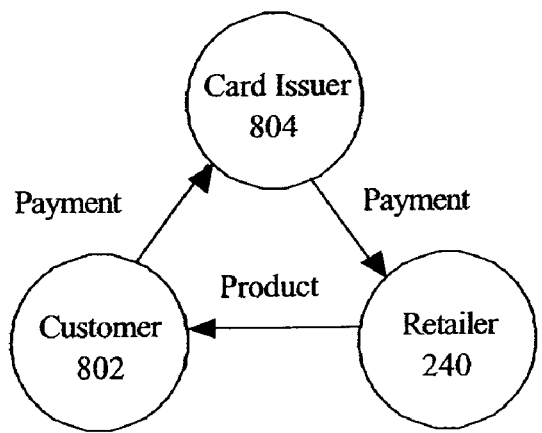
Fig. 17
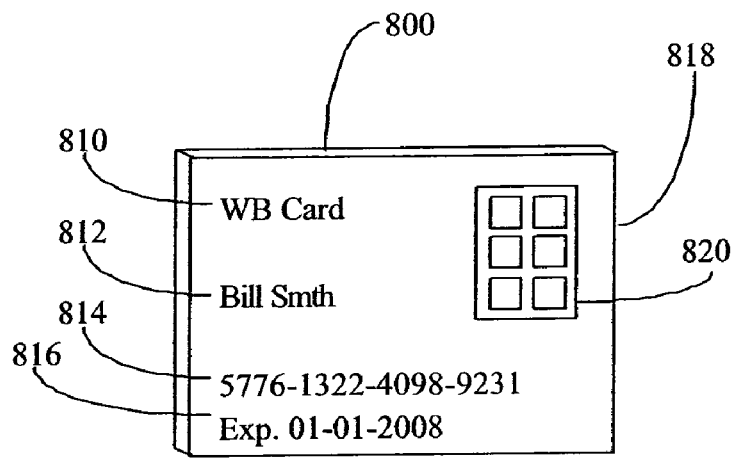
Fig. 18
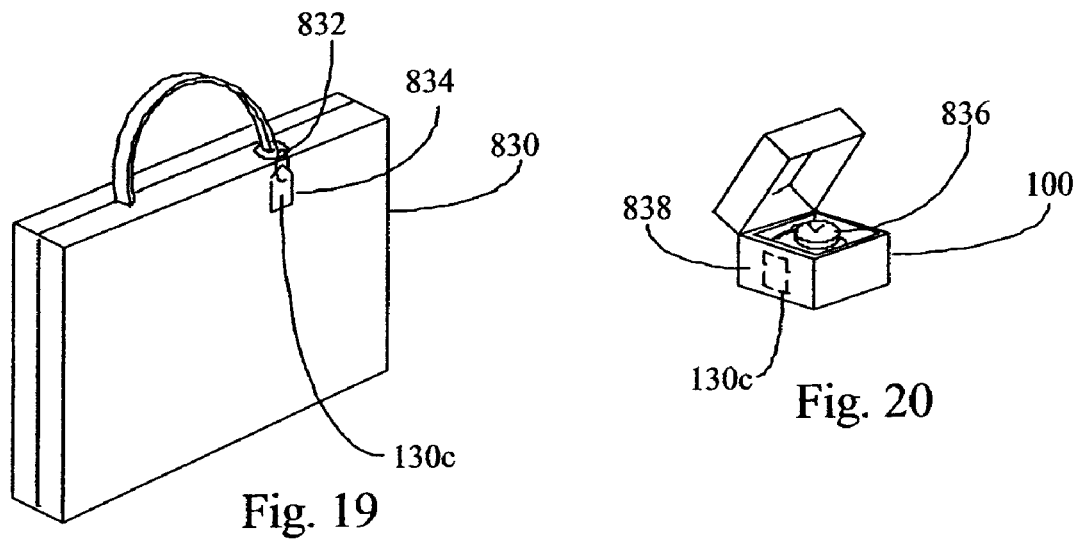
Fig. 19
Fig. 20

METHOD AND SYSTEM FOR TRACKING AND VERIFYING MEDICATION

CROSS-REFERENCE TO RELATED APPLICATIONS

This application is a continuation related to the earlier filed patent application entitled "Method and System for Tracking and Verifying Medication" which was filed on Sep. 7, 2005 and which has a Ser. No. 11/220,426 and is also related to a provisional patent application entitled "Method and System for Tracking and Verifying Medication" which was filed on Sep. 7, 2004 and which has a Ser. No. 60/607,551.

STATEMENT REGARDING FEDERALLY SPONSORED RESEARCH OR DEVELOPMENT

Not applicable.

BACKGROUND OF THE INVENTION

The present invention relates to determining when a product or medication has been distributed or dispensed properly. This is done in part by associating a unique code with each product or medication container, registering information about the product or medication and the code in a database, and subsequently using the code to retrieve the information about the product or medication. The invention also relates to enabling a healthcare worker or patient to verify that a medication has been properly distributed and dispensed.

As an initial matter, in the interest of simplifying this explanation and unless indicated otherwise, the description which follows describes the invention in the context of a medication manufacturer, medication distributor, pharmacy and patient home. However, it should be recognized that the invention should not be so limited and clearly has applications which are outside medication, only some of which are specifically discussed hereinafter.

Many industries have been plagued by fraudulent products being introduced into the market. Examples of this include the clothing of fashion designers, airplane maintenance parts, and recently, prescription and non-prescription medication. Fraudulent or mislabeled medications threaten the public's faith in the over $150 billion medication industry by misleading them to believe that a medication is what it says it is, for example the medication they are taking may actually be a sugar or flour pill with no ability to treat the patient's condition. In other cases a mislabeled medication can actually make a patient's condition worse or cause life threatening reactions.

To counteract this problem, a number of solutions have been proposed, each with a characteristic that attempts to deal with the problem, but none have created a reliable and easy to use system to prevent fraud, mislabeling, or redirection of medication in the supply and dispensing channels. For example, recently some pharmaceutical manufacturers have told their distributors that they will no longer ship products to them unless they agree only to purchase medications directly from the manufacturers. This directive potentially prevents fraudulent medication from entering the distribution channel by being traded from one distributor to another, but it already is unlikely that our country's quality medication distributors allow any fraudulent medication to enter their channel. It is also unlikely that large pharmacy chains that manage their own distribution centers would tolerate purchases from any source other than the original manufacturer. In fact many pharmacy chains purchase their own private labeled generic medication directly from qualified manufacturers, e.g. over the counter medications. In many cases fraudulent medication gets to a pharmacy via smaller or sub-distributors or by trading medication from one healthcare facility or pharmacy to another or by fraudulent substitution in the supply chain.

For years medication manufacturers have placed company or product logos on their packaging. These of course are easily copied by contemporary computer scanners and color printers. It has even been suggested that companies place on the Internet examples of the correct labeling and package appearance for their products and examples of fraudulent labels and packaging (when they have been detected). Needless to say busy pharmacists do not have the time to review a "Most Wanted Criminal" type posting for each fraudulent medication label or package on the Internet. Furthermore, this would only work for the most obvious of medication label or package defects. A system that ignores the threat posed by artfully reproduced labels and packages will only continue to expose the public to dangers, and potentially decrease safety by creating a false sense of security).

Another solution that has been proposed is to place holographic tags on medication containers, similar to those found on many credit cards. This creates an aura of protection it is largely illusionary. These proposals allow every pharmaceutical manufacturer to use whatever hologram design they choose. A pharmacist who wants to dispense a medication would have to be schooled in matching several hundred such tags manufacturers might use against the tag they see on a medication container they have selected. On top of this problem there are companies that will create imitation tags that to the casual observer might look legitimate, but aren't. In general, any solution that requires the healthcare worker to visually arbitrate the authenticity of a tag or special mark is unlikely to succeed. This is further compounded by the fact that pharmacists are in short supply and have no time for other activities beyond dispensing the growing number of prescriptions.

Other proposed solutions include placing special chemicals or markers on the labels or inks that are used to identify medication containers. The chemicals can be excited when exposed to certain light sources, e.g. ultraviolet light or a laser of a specific frequency, to reveal a hidden message or symbol. These solutions not only require more time of the pharmacist, but have the further problem of requiring the pharmacy to purchase special equipment to excite the chemicals.

Some solutions require testing the plastic or glass of a medication container by a laboratory to determine if minute amounts of chemical tags are present. Needless to say these are not solutions that offer immediate confirmation for the pharmacist.

All of the above solutions do not offer the distribution channel the opportunity to verify that medication they are handling is legitimate. For example a distributor of medication would have to open a box of medication to verify that each container within the box has been properly labeled with a tag, reactive chemical, or other special marking. One solution to overcome this concern has been to apply passive radio frequency identification tags (RFID) to each medication container. Such tags can be provided as read only tags (e.g. programmed by the silicon electronics manufacturer) or a single write tags/read many times or read/write multiple times (e.g. programmed by the pharmaceutical manufacturer) tags. These tags can generally be read through a box to determine what medication is in that box, which is better than the other proposed solutions.

One example of a RFID tag standard is the EPCglobal standard (see http://www.epcglobalinc.org/standards technology/specifications.html or EPC™ Tag Data Specification 1.0 for more information). Tags using this standard can be read by a wide variety of readers and are designed so as to identify a specific serial number (e.g. a container number) of a product made by a manufacturer. This is done by EPCglobal providing a table that converts a Domain manager number (a portion of the RFID tags contents) to a manufacturing company name. The company corresponding to the Domain Manager can then use other information in the RFID tag to determine the product name/type and a product serial number. RFID tags give the appearance of being harder to reproduce than logos or bar codes, although simple EPCglobal tags can be copied or emulated by adept electronic engineers. And therefore do not offer sufficient protection to prevent fraudulently labeled products from entering the distribution channel.

Furthermore, none of the medication container verification techniques allows the consumer to determine that the medication that has been dispensed to them corresponds to the medication that was supposed to be provided them, nor to determine the status of the medication (e.g. recall status, that the medication was originally shipped overseas, or that the bulk container used by the their pharmacy to dispense medication is registered in duplicate with one used to dispense medication in another state indicating that one of the bulk containers is fraudulent).

By way of comparison, another field that is concerned about verification of a "product" is the credit card business. In this case a credit card with an embossed number is prepared by a bank and is given to consumers. The consumer, when they purchase an item gives their credit card to the retailer for verification and transaction approval. While the credit card may have a picture of the consumer printed on it and/or a holographic picture placed on it, the retailer must verify the credit card number as well prior to proceeding with the transaction. The retailer does this by reading the credit card number (typically using a reader to read the magnetic strip on the rear of the card or by visually reading the numbers and manually typing them into a keypad) and then transferring (e.g. telephone line or dedicated network link) the credit card number, the amount of the purchase (and sometimes the item being purchased), and a retailer identification number to a credit card verification computer system. This system may be a single system (e.g. the one used by American Express) or a centralized system that refers to the member banks' computers to determine the account status (e.g. VISA or Master Card). The verification system checks the credit card number to determine that it has been issued to a consumer (elimination of fake numbers or numbers associated with a different credit card company), to determine the status of the account (has the consumer paid their bills or has the consumer reported the card stolen or lost), and to check that the retailer is registered with the credit card company (invalid retailers can be eliminated this way).

When the credit card verification computer system determines that all checks have been passed, an approval message is returned to the retailer and the purchase can be concluded by the consumer signing the credit card receipt. If the computer system determines that one or more of the checks fails (the purchase amount is greater than a limit, the account balance has not been recently paid, or the card reported lost) the transaction will not be concluded. If the credit card has been reported lost or stolen, the retailer may be requested to retain or quarantine the credit card.

The credit card verification process, while instructive, is not capable of dealing with the dispensing and tracking of medication. For example, the consumer is given a single credit card and number, which the consumer retains and guards, for multiple transactions. In the case of medication the consumer is provided with multiple medication containers over time, each of which should be separately and uniquely authenticated.

By way of further comparison, another field that is concerned about verification of a "product" is the software industry which has developed methods to verify that fraudulent copies of software are not registered or verified. One scheme has been to distribute software on CD-ROM disks with a unique registration code that is included with the labeling of the CD, e.g. printed on the CD jewel case folder or written directly on the CD label. The user installs the software on the CD onto their computer and is then requested to enter the registration code as part of the installation process. The user enters the code, which is verified by the installation software or is sent to a remote verification system. If the code is not verified as being a correct code the installation is terminated. If the code is sent in duplicate to a verification system the system will refuse to install the software unless it is being "re-installed" on same computer on which it was originally installed.

While instructive, this form of a product verification system has four weaknesses; one it requires that the person using the registration system perform a software installation before the authenticity of the software has been verified; two it allows anyone to attempt to enter and verify a registration code; third it does not provide the consumer with information that they can use to verify that the product is correct other than the response of the registration system that the registration code is correct or not; and lastly it does not provide for dispensing a portion of the software product with a new code that can be verified by the consumer.

None of the above solutions allow the patient or consumer to determine that medication that has been dispensed to them is authentic, as none of the medication container labeling schemes can be readily verified by the consumer. This is especially the case when medication is dispensed by transferring it from one container (e.g. a bulk bottle) to another container (e.g. a vial, blister, or packet).

Thus, it would be advantageous to have a medication labeling and verification system that can be used at any point of the distribution, dispensing, and consuming process. Such a system would need to be easy to deploy using existing technologies and use container labels that are easily detected when a fraudulent medication has attempted to be verified.

BRIEF SUMMARY OF THE INVENTION

The present invention relates to a product or container labeling and verification system that uses unique codes applied to the product or container and registers those codes with additional product information in an accessible database. The code can be used so that the product information can be updated with additional information related to the product being shipped, dispensed, or consumed so as to accumulate a life history of a product. The code can be used to retrieve portions of the product information and portions of any additional information related to it that can be used to determine if the product is legitimate, fraudulent, or possibly fraudulent. In some cases information about a fraudulent or possibly fraudulent product is sent to the product manufacturer, re-packager or dispenser, or a regulatory agency for investigation.

In one embodiment, the invention is largely limited to transactions between pharmacies and their customers as recorded in a database. In this case the pharmacies provide coded (usually uniquely coded) medication to their customers.

In another embodiment, a bulk medication container is labeled conventionally with text describing the medication. The container is also labeled with a unique container code number. The container code number can be in the form of a text string, a bar code, or as an RFID tag. While not required it is preferable that the container code number be issued in a unique, generally non-sequential or random-like manner, so that valid code numbers can not be easily guessed. For example, a code of seven alphanumeric characters allows for nearly three trillion combinations allowing only a one in three million chance of guessing a correct container code for when a million container are manufactured over 10 years.

The manufacturer enters into a secured communication with a database by providing a password, cookie, special virtual private network, code or key that is unique to each manufacturer. This prevents unauthorized groups to pose as a manufacturer and interact with the database. Each container code number is then entered into a database along with a description of the medication (medication information) which may include the medication name, size or concentration, form (blue pill, fluid bag, green tablet, etc), lot number, expiration date, and other useful information. Furthermore, additional container status information can be added to the database, such as its shipping destination (e.g. ABC Distributors in Illinois or XYZ Distributor in Poland), information about tracking it during distribution, which pharmacy received it, that there is a concern that the medication in this container may be fraudulent, and other information about the medication.

The database can be maintained by each pharmaceutical company for its own medications or can be linked together or shared by several manufacturers at or through a centralized verification system.

In some cases several medication containers are placed inside a single shipping box. The box itself can be labeled with its own container code. This container code and information about the box and its contents are entered into the database. When a RFID tag is used to store the container code on each container, a box level container code may not be required as the container code(s) can be read through the box.

When a RFID tag is used, the container code can correspond to the EPCglobal standard. However; to improve security, the RFID tag can be equipped as a secure tag, one that will not reveal information within it unless it first receives a properly encrypted key to access information and/or one that only sends the container code in an encrypted format. This prevents anyone from readily reading or copying its contents to another tag. In some cases the RFID tag can also have recorded in its memory portions or all of the above described medication information.

When a box holding one or more containers is received by a distributor, the container code of the box is read and entered into a data retrieval program. When the RFID tag is used to label each container in the box, the container codes of each container in the box can be read and entered as part of a data retrieval program. When the distributor only receives a single bulk medication container the individual container code can be read and entered into a data retrieval program.

When the container code is text, the code is read by a worker who enters it into a keyboard. Alternately, a computer can scan the container code and use optical character recognition software to recognize the code and enter it into a data retrieval program. When the container code is a bar code a bar code reader can be used to read the code and when it is a RFID tag a tag reader can be used to read the code. The later process may require the transmission or presentation of a special or encrypted key to the RFID Tag in order to gain access to the code. In either case the code is presented to a computer which uses it as part of a data retrieval process.

The data retrieval process includes sending a container code to a verification system, for example by using the Internet or a private network. The verification system may be configured as a single server, multiple servers, or a server(s) for each manufacturer. Optionally, a distributor identification code is also sent to the verification system. The verification system can first determine that the identification code corresponds to a recognized distributor, if not an appropriate error message can be returned to the requester. Furthermore, the container code, if any is provided at this point, can be marked as suspicious, having originated from an unregistered source.

Provided the distributor identification code is recognized, the verification system can provide to the database the container code(s). The database then checks to see if the code has been entered into the database. This may entail the verification system determining which manufacturer made the medication in the container and then requesting the manufacturer to verify the remaining portion of the container code. If the container code is not entered into an appropriate database, then an error message is sent back to the requestor indicating that the provided container code is not entered into the database and the container and its contents should be quarantined for additional inspection as a counterfeit. The verification system can record in a database the date/time, distributor identification code and container code for later checking that the container was quarantined.

When the container code does match one that was entered in the database, a positive match is indicated and some portion of the medication information is retrieved and presented to a worker or automated checker at the distributor. The retrieved medication information may just indicate the name and size/concentration of the medication which can be verified with the container's label (textual, bar code, or RFID). Should the medication information not correspond to the label an error can be indicated by the worker or automated checking machine to the verification system. At this point the container should be quarantined, the verification system should provide a warning to the manufacturer corresponding to the container code that a container code that was entered in a database has been used to label a container that does not contain the appropriate medication. Similarly, a portion of the container status information can be retrieved, presented and checked. For example if the container was marked as shipped to Poland, but the distributor is located in Illinois an error in the use of the medication can be determined by either the verification system or the distributor. In this case the manufacturer may notify the distributor to quarantine or remove the container from use or to send it back to the manufacturer for inspection.

Should the medication information indicate that the medication has exceeded its expiration date the worker or checking machine can be notified to quarantine the container. Similarly, the lot code of the medication information or the container code can be used to check with the manufacturer (or other responsible authority) to determine that the medication has been recalled and the container should quarantined, e.g. as part of the container status information.

When the medication information matches with the container label and any additional status information is checked, the distributor identification number can be entered in the database as part of the container status information for the container code.

When the medication container is moved from one distribution center to another, the container code can be checked and verified along with other information and the distribution identification number or each distributor receiving the container and the date of receipt can be entered in as additional status information for the container code.

In another embodiment the checking of container codes by the distributor may be performed but is optional. In this new embodiment the pharmacist, when receiving a medication container and placing it into inventory, can read the container code and send a confirmation request to the verification system along with the pharmacy's identification number, code, or password. As before, the container code can be text in which case it is entered into the pharmacy computer via a keyboard or read by an optical character reader, it can be bar code and read by a bar code reader, or it can be a RFID tag and read by a matching reader (the reader can provide appropriate security keys or encrypted message to the RFID tag in order to obtain the code). This parallels the same activity described for the distributor.

The verification system checks the pharmacy identification, when it is invalid, an error is indicated to the pharmacy and another error message can be sent to other interested parties. When the pharmacy identification number is verified, the container code is checked to see if it has been entered into a medication container database maintained either by the verification system or the manufacturer. If the container code is not recognized an error message is sent to the pharmacy that the container is to be quarantined and another message can be sent to the manufacturer that a container code associated with that manufacturer has been located at the pharmacy, but the container code was not located in the appropriate database.

When the container code is located, all or a portion of the medication information is sent to the pharmacy allowing a pharmacist or other worker to verify this information with the container's label (this can also be done by a label optical character recognition program). The pharmacist can also open the container to determine that the medication that is claimed to be in it actually matches the medication information. Any discrepancy can be indicated back to the verification system. The pharmacy then quarantines the container and the appropriate manufacturer and regulatory agency can be notified that a counterfeit medication has been discovered at this pharmacy.

Similarly, a portion or all of the container status information can be presented to the pharmacy for verification. For example the pharmacy is located in Illinois, but the status information indicated that the container was sent to Poland. In this case the verification system or the pharmacy can detect this error and send a message to the manufacturer that a specific container of medication was diverted from one market to another. The pharmacist can place the container in a quarantined status.

Similarly, if the status information indicates that the same container code was received by another pharmacy a potential error is indicated to the pharmacy and the manufacturer. While this may not be an actual error as it is possible pharmacies may at times trade medication to balance inventories or to prevent expiration dates from being exceeded. However, to detect counterfeit medication the verification system can contact the pharmacy originally associated with the container to determine that they traded or exchanged the medication container with the new pharmacy. Should the original pharmacy be unable to determine that the medication was exchanged; the new pharmacy will be sent a message to mark the medication as suspect. If the original pharmacy still has the container, a new message can be sent to both pharmacies indicating that one of them has a counterfeit medication container and that both should quarantine the containers. The medication manufacturer can be sent a message indicating the two pharmacies that have medication containers labeled in duplicate. As desired a regulatory agency can be contacted to determine the status and origins of the medication containers. If the original pharmacy no longer has the medication container, but did not exchange it (e.g. all the medication was dispensed and the container was thrown away) the new pharmacy and the manufacturer can be sent messages to quarantine the medication container.

Should the medication information indicate that the medication has exceeded its expiration date the pharmacy can be notified to quarantine the container. Similarly, the lot code of the medication information or the container code can be used to check with the manufacturer (or other responsible authority) to determine that the medication has been recalled and the container should be quarantined.

If every check passes the pharmacy can dispense medication from the container and the pharmacy identification number is entered into the additional information section for the container code. When a read/write RFID tag is used to store the container code, the verification system or manufacturer can generate and send a registration code that is written to the RFID tag. The RFID tag can be read as well to verify the write operation. Alternately, the registration code is recorded by a pharmacy computer. The registration code is used to indicate that this container has been received by the pharmacy in the instance that the container code is not to be verified again. The registration code is preferably unique, generally non-sequentially generated so as to make is difficult to guess valid numbers. The pharmacy identification number is typically added to the mediation status information.

The pharmacy can check the container code with the verification system either once when the container is received, when medication is first dispensed for a patient, or it can be checked every time medication is dispensed. Checking the code every time medication is dispensed is one way for the pharmacy to determine if another medication container with the same container code has been detected elsewhere. The pharmacy may also receive error messages about the same container code being read by another pharmacy by e-mail whenever this situation is detected by another pharmacy trying to verify a medication container.

When medication is dispensed from a medication container by the pharmacy for a patient, several additional steps can be incorporated. For example, the container code can be verified with the verification system as described previously. Any errors can result in the medication being quarantined as described above. However, there may be situations where the pharmacy may not want to check the container code every time medication is dispensed or that the medication is not dispensed to the patient but selected by the patient (e.g. over the counter medication) and the description that follows is not dependent on the container code being checked every time medication is dispensed.

Patients may also purchase "over the counter" medication that is not subject to review by a pharmacist. In this case the container code (it is presumed each patient purchasable medication container has a container code that is at least unique to the receiving pharmacy) can be checked by the checkout station, for example by reading the container bar code or RFID tag. A portion of the medication information or other information can be checked to determine that a medication is not counterfeit or if it should be quarantined. A successful check can be indicated to the patient as part of their receipt since no additional pharmacy label is provided for medication of this type. An unsuccessful check may result in the transaction or purchase being voided or an error message printed on the customer's receipt. However, when a RFID tag is applied to the medication container the checkout station can write back to the tag an indication of a successful check or not.

When a pharmacy dispenses medication to a patient/customer the pharmacy labels the container holding the medication with a medication code. The medication code is similar in purpose to the container code with a few exceptions. The medication code number can be in the form of a text string, a bar code, or as an RFID tag. While not required it is preferable that the container code number be issued in a unique, generally non-sequential or random-like manner, so that valid code numbers can not be easily guessed. Considering that over 2 billion prescriptions are filled every year (and increasing) provision should be made that over 60 billion pharmacy labels will be provided on containers during the next 20 years so an twelve alphanumeric character code allows only a one in two million chance of guessing a correct medication code. An alternate would be to use the container code (on or from the bulk medication container used to dispense the medication) as the medication code for each prescription dispensed from a single medication container. Note when two medication containers are used to fill a prescription both container codes will be needed to be recorded.

The medication code (or container code as appropriate) is then entered into a database along with pharmacy dispensing information. The dispensing information includes information such as the date the medication was dispensed, the name or other identifier of the pharmacy that dispensed the medication, the amount of medication dispensed, and either the container code or a portion of the medication information which may be obtained directly from the medication container label or by using the container code of the dispensed medication to download or link to the medication information. Generally, to protect patient privacy the patient name or other patient identifier is not entered in the database, but if desired it or a proxy for it can be.

When medication is dispensed, the container in which the pharmacy received the medication may be given directly to the patient, that is the medication is not individually dispensed into a new container. For example this is the case with most injectables (frequently individually boxed, in this case the box can be the container) and prepackaged medication (such as those in blister packaging). The pharmacy typically prepares a pharmacy label for the patient/customer indicating the patient's name, the physician prescribed dosing regimen, the name of the pharmacy that dispensed the medication, and other important information. When this is done the pharmacy label may have a medication code alphanumeric text added to it. When there is a container code on the container provided to the patient the container code can be used as a medication code. The medication code is entered into a database of a verification system which may be the same one previously described or one that is run specifically for the interests of patients, e.g. operated by the pharmacy.

Besides or in addition to printing medication code text on a label the medication code can be printed on the patient's receipt for their purchase. Preferably the receipt will include the medication name with the medication code. If the container information has not been verified with a verification system, a notation of this can be included or it may also be indicated by not printing a medication code on the receipt.

When the patient returns to their home or other location where they may consume or inspect their medication the patient can use a computer to request information about their medication by entering the medication code into a computer, for example by typing it into a keyboard or reading it with a bar code reader or RFID reader as appropriate. To facilitate this process the patient may access a data retrieval web page via the Internet. Entering the medication code will request a portion or all of the stored pharmacy medication and dispensing information to be retrieved. The patient can then verify this information as a means to determine that the medication was properly dispensed for them and that the medication is likely genuine or possibly counterfeit. For example, if the medication code has not been entered into the on-line accessible database it is likely the medication was not properly dispensed or the patient improperly entered the medication code. The patient may be requested to reenter the information to double check it or to identify themselves for additional inquiry. If the medication has exceeded its expiration date or is subject to a recall notice additional error messages can be sent to the patient by accessing container status information related to the container code.

The on-line database may also provide portions or all of the medication information and status information to allow the patient to compare that the medication dispensed to them corresponds to the medication they were to receive, for example the medication name and a picture of the medication can be provided. If this information does not match the medication received, the patient can indicate this error by to the on-line database which can forward this information back to the pharmacy for additional analysis or as appropriate to the manufacturer or a regulatory agency. For example if the medication information indicates it was shipped to Poland, but was received by the patient in Illinois, the patient or the on-line database system can trigger an examination of how the medication was diverted to this pharmacy. Other errors can be detected such as when the medication code was indicated as being received by one pharmacy, but has been dispensed by another. Some of these errors can be detected if the pharmacy verifies the container information for the medication when dispensing it. However, in some cases the pharmacy may not verify the container information every time medication is dispensed.

In another embodiment that can be used in conjunction with the above steps or separate from them, the pharmacist dispenses medication for a patient into a medication container and provides a medication code that is associated with at least a medication identifier, both of which are provided to the patient. For example the medication code can be provided to the patient by printing it on a label (e.g. as text, a bar code, or part of an RFID tag) attached to a medication container and where the container or the label included the medication identifier (e.g. preferably the medication name, but may include the medication size, concentration, lot number, prescription regimen for the patient). Alternately the medication code and medication identifier can be printed on the receipt given to the patient.

The pharmacist also enters the medication code number into a database along with or linked to medication information. The medication code is selected so as to be unique and preferably non-sequential or random in order as previously described.

The patient when at home or at a location where he can access a computer network (e.g. Internet access) can enter the medication code (e.g. by typing the code, reading the bar code or RFID tag with an appropriate scanner) into a software program that accesses the database maintained by the pharmacy (e.g. www.jonespharmacy.com) or by a centralized verification system (e.g. www.mymedication.com). The database retrieves the stored medication information and can use the medication code or the medication identifier to obtain additional container status information (expiration information, recall information, shipping information, receiving information, and other information about the medication status) from the same or other databases. If the medication code has not been entered in the database an error is returned and the patient may be requested to reenter the medication code (perhaps a typing error occurred). Alternately the patient should consider reporting this error to the pharmacy where the medication was dispensed when the entered the medication properly or report it to a regulatory agency. The medication verification system can also report the error, but since the system may not have enough information to identify the person providing the errant medication code due to patient privacy issues (e.g. HIPAA legislation) and the verification system may not have been provided with a valid pharmacy identifier. If the patient is registered with the database their identity or virtual identity can be determined so as to create level of trust to ensure that no one is probing the database to surreptitiously locate valid medication code.

Portions or all of the retrieved information are transferred to the patient's computer for review. The patient can then verify that the medication sold or provided by the pharmacy corresponds to the medication they have. For example that the medication name on the container label matches the one retrieved from the database, the size or concentration is the same, or the shape and color of the medication matches a picture provided by the database. If something doesn't match the patient can contact their pharmacy, a regulatory agency, or the verification system administrator, or the medication manufacturer. The patient can also use the container status to determine that a medication should no longer be consumed (e.g. it has exceeded its shelf life or has been recalled). The patient can also determine that there may be problem if the medication information or container status indicates that the medication was dispensed by a different pharmacy than the one that dispensed their medication or that the medication had been shipped to another country. Again the patient can notify a variety of parties to determine if the medication should be discontinued, returned, replaced and to provide notice that similar medication dispensed by the pharmacy may need to be quarantined by other patients.

Of course there need to be appropriate safe guards that valid medication codes in the database cannot be determined by sequentially providing generated medication code numbers to see if any are registered. With high speed network connection to the Internet it may be easy to determine previously registered medication numbers. This can be averted by requiring each patient to register with the verification system with a name (or alias) and password so any mass probing activities might be detected and stopped. Alternately, the computer may require a person to recognize and enter a code that is merged with a picture. This has been used by others to prevent automated computer probing of computer systems.

The verification system above can also be used to guarantee the authenticity of other products purchased by consumers. This can be of importance to high value products (designer apparel or accessories) or products (e.g. DVD movies) where the manufacturer is concerned about fraudulent or counterfeit products being sold.

For example a credit card or other financial transaction company can provide insurance that a product is authentic when codes are verified with each product purchase. For this purpose each product a manufacturer makes can have a unique and hard to guess product code which is entered into a verification system database when manufacturer properly identifies themselves to the verification system. Prior to selling a product to a consumer the retailer reads the product code and presents their identity (e.g. password or other method to electronically enter into a trust relationship) and product code to a verification system. When the product code is recognized by the verification system information about the product is provided to the retailer so they can determine that the product is the same as the provided description. If there are any errors the retailer is asked to quarantine the product for further investigation by the verification system or manufacturer.

Assuming no errors are detected information about the customer is provided to database. When the verification system is run by a credit card company, this can be facilitated by reading the customers credit card. Once the transaction is approved a receipt is prepared for the customer with a unique and hard to guess verification number printed on it for each product for which a product code was checked.

The customer then takes the product home and can gain access to the verification system (e.g. via the Internet) by providing a password, account number, cookie, or other access key. The customer enters the verification code from the receipt and the verification system then determines that the verification number has been entered into its database. If not the customer is asked to return the product and receipt for a refund as the verification system cannot determine that it is genuine. The verification system also provides information about the product for the consumer to review. If this information does not match the product they purchased, the consumer can indicate this to the verification systems and return the product to the retailer for a replacement or refund. The verification system can then investigate how this happened to prevent this problem from being repeated.

The verification system also checks to determine if a product with an identical product code or verification number was sold to a previous customer. If so the customer is asked to return their product with product code and receipt to the retailer for an investigation. If the product is not authentic the customer is given a replacement product or refund. When either the verification code or product code is associated in the verification system with another customer that customer can also be instructed to return their product, product code and/or receipt for investigation to the retailer or another agency for investigation. If the product the other customer has is not authentic it can be replaced or a refund provided to that customer. In this way any customer is protected from purchasing a fraudulent product and it they do they are reimbursed for their expense.

When a retailer is asked to refund the purchase price of a product that had previously been verified the retailer is protected from financial loss by the verification system company (e.g. a credit card company) or by the manufacturer. The credit card company or other agency to provide this authentication and warranty service can be paid by the manufacturer of a product, the retailer selling product, or the customer purchasing a product. The process of assuring and insuring that only authentic products are sold is based the difficulty of any retailer or customer has to guess a valid product code or verification code (which can be substantially increased when either one is recorded in a secure RFID tag) and the number of different checks performed (the retailer and the customer). Even when only a few customers check the verification number they are provided on their receipts, the interests of all customers are served by keeping the retailers on guard for fraudulent products.

BRIEF DESCRIPTION OF THE SEVERAL VIEWS OF THE DRAWINGS

FIG. 4 is a table listing information stored in a verification system database for a medication container prepared by a manufacturer or repackager;

FIG. 5 is a table listing container status stored in a verification system database for a medication container;

FIG. 6 is a table listing retailer identification information stored used to identify a retailer to a verification system;

FIG. 14 is a list of errors that can be sent to a patient by a medication verification system;

FIG. 15 is a list of errors that can be sent to by a patient to a medication verification system;

FIG. 17 is schematic showing the relationships between customers, retailers and financial card companies;

FIG. 18 is a perspective view or a financial transaction card;

FIG. 19 is a perspective view of a product with a product code linked to it;

FIG. 20 is a perspective view of a product in a box where the box has a product code;

DETAILED DESCRIPTION OF THE INVENTION

The present invention may be adapted for use in a wide variety of applications and is suitable for any environment in which products are manufactured distributed, received, and then subsequently dispensed for individuated use. By way of illustration and not by way of limitation, unless indicated otherwise, the preferred embodiment is in the context of a medication tracking and dispensing system using medication containers, container codes, medication information and container status information to detect a fraudulent or possibly fraudulent pharmaceutical product prior to use or consumption by a patient. Throughout this specification, identical numbers represent similar components and symbols.

I. Hardware and Database Entries

Figure 1:
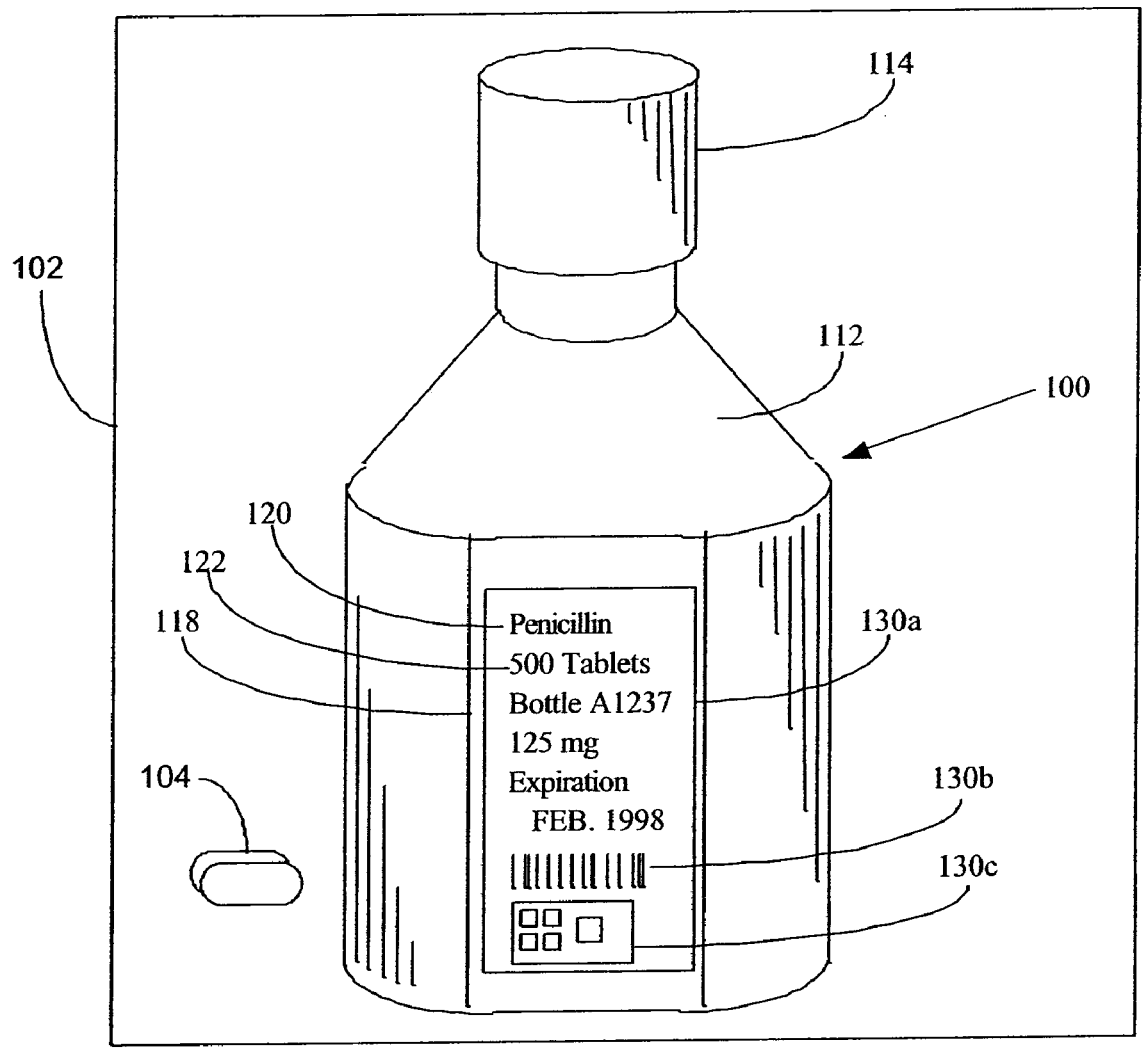
FIG. 1 is a perspective view of a bulk medication container holding loose medication doses with an identification label applied to it.
Figure 2:
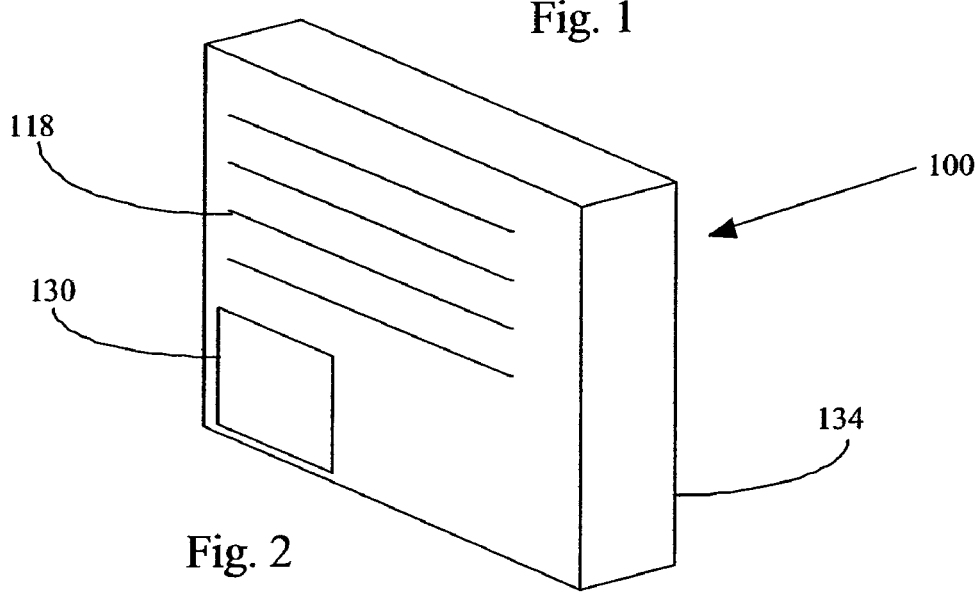
FIG. 2 is a perspective view of medication container holding prepackaged unit doses of a medication with an identification label applied to it.

FIGS. 1 and 2 show medication containers 100 as packaged by a pharmaceutical manufacturer or repackager 102. Container 100 in FIG. 1 is a conventional bulk container or bottle 112 holding individual pills, tablets, capsules, liquids, gases or other forms of medication 104. Access to the medication 104 within bottle 112 is provided by removing cap 114. Attached or part of bottle 112 is a medication label 118 on which can be printed the medication name 120, quantity of doses 122, and other readable text describing medication 104. Label 118 can include also include a medication container code 130, shown as a printed alphanumeric code 130a, bar code 130b, or recorded in a memory device or tag 130c, e.g. a radio frequency identification tag (RFID) or any other wireless access memory device, FIG. 2 also shows container 100 but now in form of a prepackaged container 134 that can be sold to a patient. Medication 104 inside container 134 can be blister packed or within a bottle, a single syringe, ampoule, inhaler, or other sub container. Container 134 also has medication label 118 and medication code 130.

Figure 3:
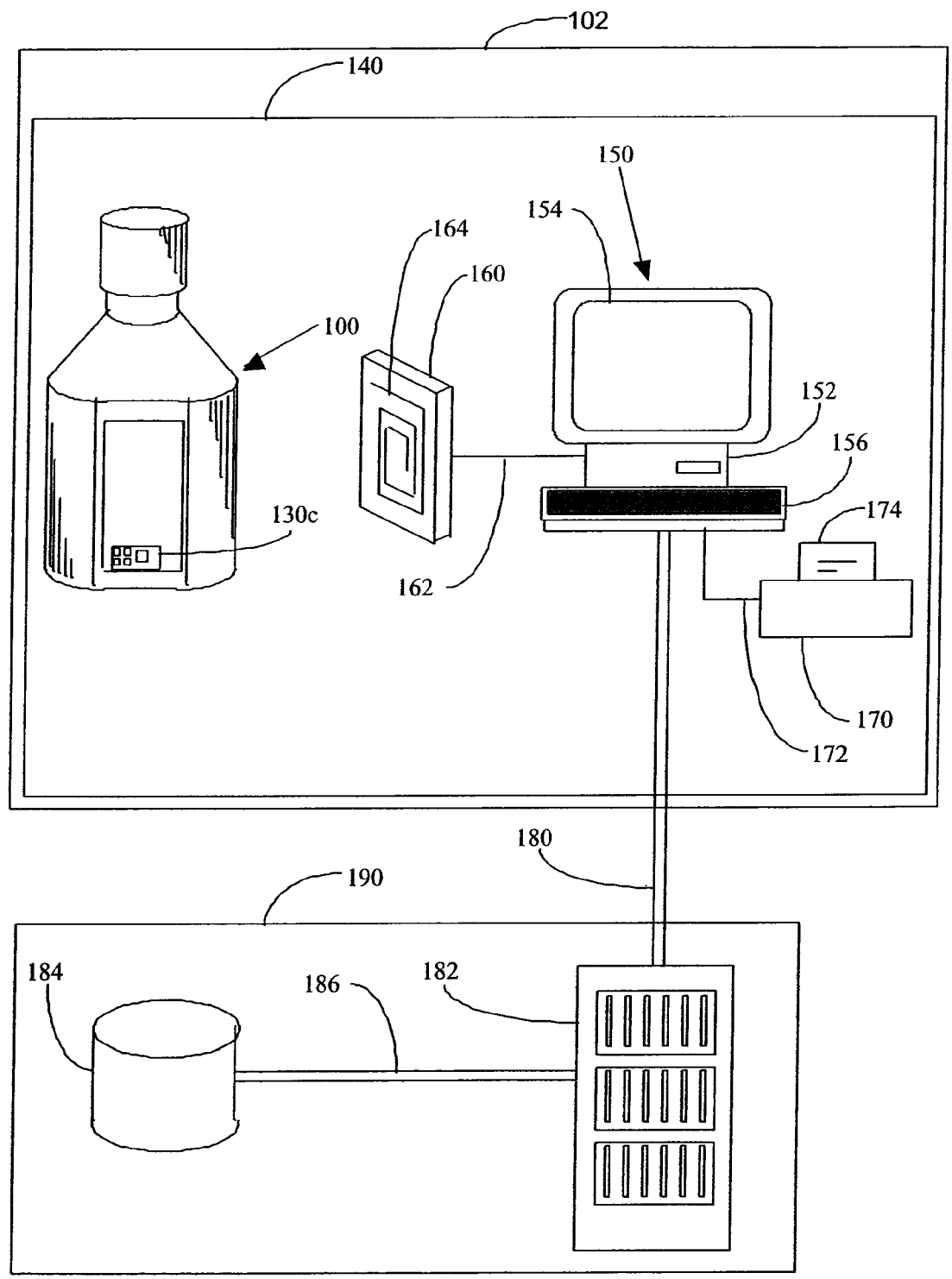
FIG. 3 is a schematic view of a computer system that is used to read medication label information, enter or retrieve information from a database and print appropriate labels or receipts.

Referring to FIG. 3, a manufacturer or repackager 102 uses data recording and preparation station 140 is shown. A medication container 100 is brought to station 140 either after being filled or before being filled. Computer 150 controls preparation of container code 130. Computer 150 is comprised of a CPU and memory 152 linked to a display 154 and a keyboard or mouse 156. CPU 152 is also linked to transducer 160 used to read container code 130 via communication channel 162. As shown transducer 160 can include a RFID tag reader 164 (and writer when needed). CPU is also linked to printer 170 via communication channel 172. Printer 170 is used to print text documents 174 or container label 118.

Computer 150 is further linked via network 180 to a data retrieval server 182 which in turn is linked to database(s) 184 via communication channel 186. While server 182 is shown as part of a remote medication verification system 190 it can be part of computer 150. In other instances system 190 can be operated by an independent service that supports the needs of several manufacturers 102. To communicate with verification system 190 manufacturer 102 can be required to enter a password, code or other method of identifying themselves a trusted partner.

In the following discussion the words "enter", "register", or "record" refer to the process of inserting information into database 184 or other database and the past conjugates of these words refer to information that has previously been inserted into or known to database 184. It is generally assumed that any information in database 184 was inserted there as part of a communication with a computer or person that has identified themselves. The word "link" when used regarding items or logical records of database 184 means to make a logical connection between one item or logical record in database 184 to another in database 184 or another so that at least one item has the attribute that when it is presented to database 184 the other item or logical record, or information about it can be retrieved. The word "linked" means having previously established a link between two items. The word "access" when used regarding items or logical records in database 184 or other means to identify an item and have it retrieved for review, presentation, analysis, or other computing activities.

In some instances label 118 is prepared by computer 150 using printer 170 prior to container 100 being filled. Label 118 is applied to container 100 or in some cases printer 170 can print directly on the surface of container 100 (e.g. when container 100 is paper box or printer 170 is a laser capable of directly writing a readable image on the exterior of container 100). In other cases computer prepares label 118 only after container 100 has been filled. In either case a container code 130 is prepared and either written as part of label 118 (text or bar code) or written to RFID tag 130c using transducer 160.

Container code 130 is a unique code for each medication container 100, however when multiple containers 100 will be delivered to the same pharmacy as part of a shipping package they may all share a single container code 130. Container codes 130 are preferably issued in a unique and random-like or at generally non-sequential manner so as to make it difficult to guess a valid code, for example a twelve character alphanumeric code will produce over 96,000 trillion combinations, so that it is very difficult (e.g. less than 1 out of a million over the course of 10 years of medication manufacturing) to guess any individual valid code. Each container code is entered into database 184 with medication information 200 (see FIG. 4) so that by providing container code 130 information 200 can be retrieved. Medication information 200 can include medication name 120, medication manufacturer information 211 (e.g. name, identifier, and contact information), medication size/concentration 212, form/shape 214, the quantity of medication 215 initially in medication container 100, manufacturing lot number 216, expiration date 218, and other data relevant to the medication at the time of manufacturing.

Information 200 can also be accessed by container code 130, or in some cases by medication name 120, and/or lot number 216. Similarly, code 130, name 120, or lot number 216 can be used to add information about a medication 104 to server 182 or database 184. When or after medication container 100 is shipped to a distributor or pharmacy 240 (see FIG. 7) additional information can be stored in database 184 or linked to database and is referred to as container status 220 information (see FIG. 5). Status can include the destination 222 to which container 100 was shipped, the pharmacy 224 that received container 100, the recall status 226 of the medication 104, new contraindications 228, container code error flag 229 (e.g. container code 130 was reported received by another pharmacy or other error states), and any other information about medication 104. When a medication 104 is recalled, recall status 226 can be updated by providing only medication name 120 and/or lot number 216 to server 182 or database 184.

When container code 130 is already printed (e.g. preprogrammed RFID tags) and then applied to container 100 or pre-applied to container 100 (e.g. by the container manufacturer 102), computer 150 can use transducer 160 to read code 130 (text, bar code or RFID tag) and enter it into database 184 along with medication information 200. Alternately, when container code 130 is text it can be manually entered using keyboard 156.

Referring to FIG. 6, when medication container 100 has been filled and labeled, it enters transportation system 230 and is received by pharmacy 240. Pharmacy 240 has a computer 250, which is for purposes of discussion similarly equipped as computer 150. Computer 250 is linked to transducer 260, which can be used to read container code 130 (text, bar code, RIFD tag) related to container 100. When container code 130 is text it may be entered manually using a keyboard attached to computer 250. Printer 270 is used to prepare label 306 for dispensed medication containers (e.g. container 300, note container 300 can in some cases be the same as container 100 as shown in FIG. 2) or for printing purchase receipt 320 (see FIG. 11). Computer 250 uses communication network 280 to interact with verification system 190 and database 184.

Pharmacy 240 can also use communication network 390 to enter information about medication 104 dispensed to patients into patient medication verification system 396, which may be identical to system 190 or may be a separate system with its own database maintained by the pharmacy or an independent verification agency.

When medication is dispensed and provided to the patient or guardian (e.g. inside container 300) the patient can transport 400 it to his home 410 or to any other site where he has access to a computer 450. Computer 450 is configured similarly to computer 150 or 250 with a processor, memory, display, keyboard or pointing device (not all shown). Computer 450 can be linked to a transducer 460 which can read text, bar codes, RFID tags or other information sources and is similar to transducers 160 and 260. Computer 450 can communicate via network 490 (e.g. the Internet) with verification system 396.

Figure 9:
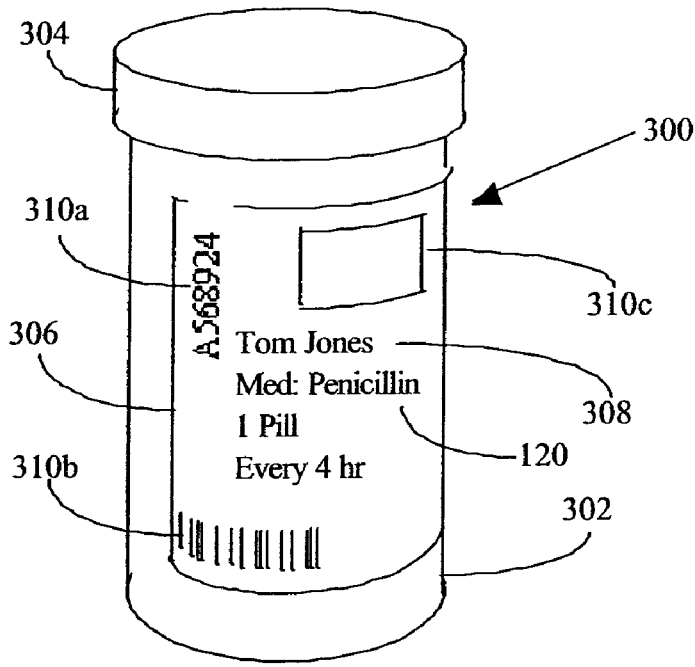
FIG. 9 is a perspective view of a medication container that a pharmacy has prepared for a patient.
Figure 10:
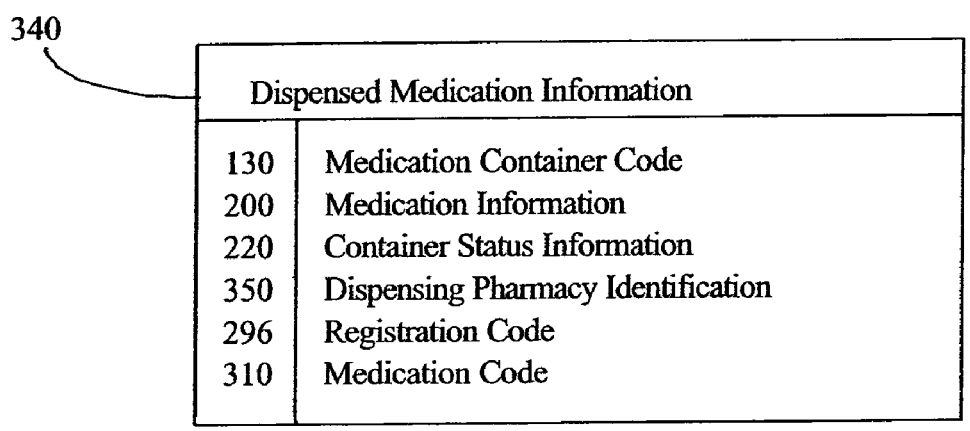
FIG. 10 is a table listing dispensed container status stored in a verification system database for a medication container dispensed by a pharmacy to a patient.

Container 300 holding dispensed medication 104 can be in a variety of shapes. As shown in FIG. 9 is can be in the form of vial 302 and matching cap 304, however, it can be a box, an ampoule, an inhaler, a syringe, etc. Container 300 typically includes a label 306 which identifies the dispensed medication name 120, the patient name 308 for whom it is was dispensed, and other medication and dosing regimen information. Label 306 can include a unique medication code 310 in the form of a text code 310a, a bar code 310b, or as a memory device or tag 310c (e.g. a RFID tag, but others are contemplated).

Medication code 310 is a unique code selected similarly to container code 130 in a unique and non-sequential or random-like manner so as to make it very difficult to guess a valid medication code number, for example only a one in a million chance in 10 years of medication dispensing with medication codes 310. When medication 104 is dispensed by pharmacy 240 medication code 310 is selected (or provided if previously recorded as part of RFID tag 310c) and entered into a database in or linked to verification system 396. Additional dispensed medication information 340 is entered or linked to verification system 396 and retrievable by medication code 310. Dispensed medication information 340 typically includes all or portions of medication information 200 and container status information 220. When medication information 200 is not available via container code 130 from verification system 190 the pharmacy can enter this information directly into verification system 396, for example by typing it or scanning it from label 118. Medication information 340 typically will include dispensing pharmacy identification 224. Other information may be included as appropriate.

Figures 11, 12, 13:
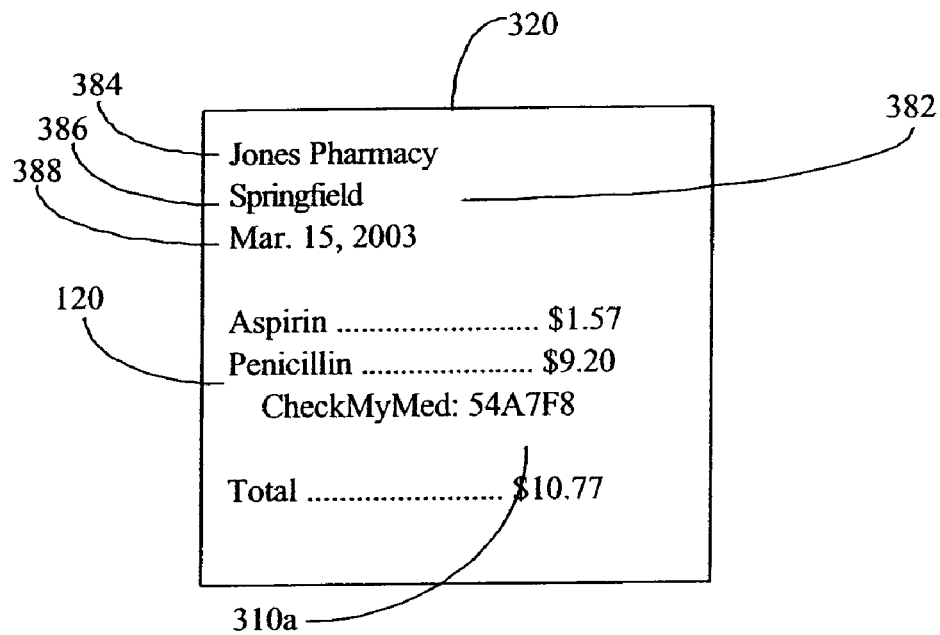
FIG. 11 is a sample of a receipt prepared for a patient including medication identifiers and medication code numbers.
FIG. 12 is a list of errors that can be sent to a pharmacy by a medication verification system.
FIG. 13 is a list of errors that can be sent by a pharmacy to a medication verification system.

FIG. 11 shows a conventional receipt 320 for the purchase of products at a pharmacy. It includes information 382 about purchase such as the pharmacy name 384, address 386, and date of purchase 388. It also indicates the name of the products purchased, e.g. medication name 120 or a medication name proxy to protect patient privacy and may further include printed medication code 310a. Receipt 320 may be substituted for label 306 for recording medication code 310, e.g. where no additional space is available for printing medication code 310 on label 306.

II. Operation of the Tracking and Verification System 190 with Container 100

Figure 16A:
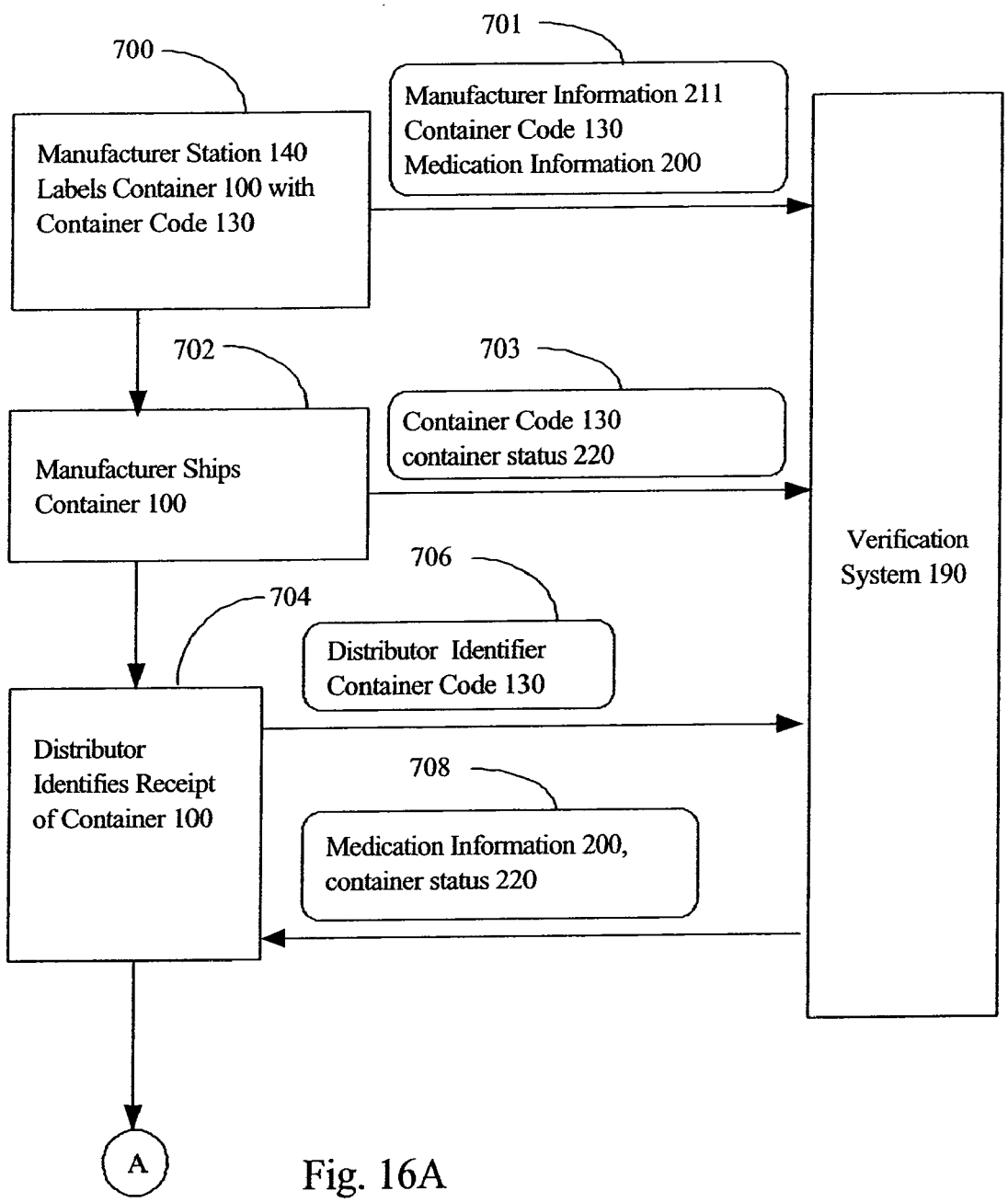
FIG. 16 is a flow chart of the steps used to track and verify medication containers as they are distributed, received, and dispensed to patient.
Figure 16B:
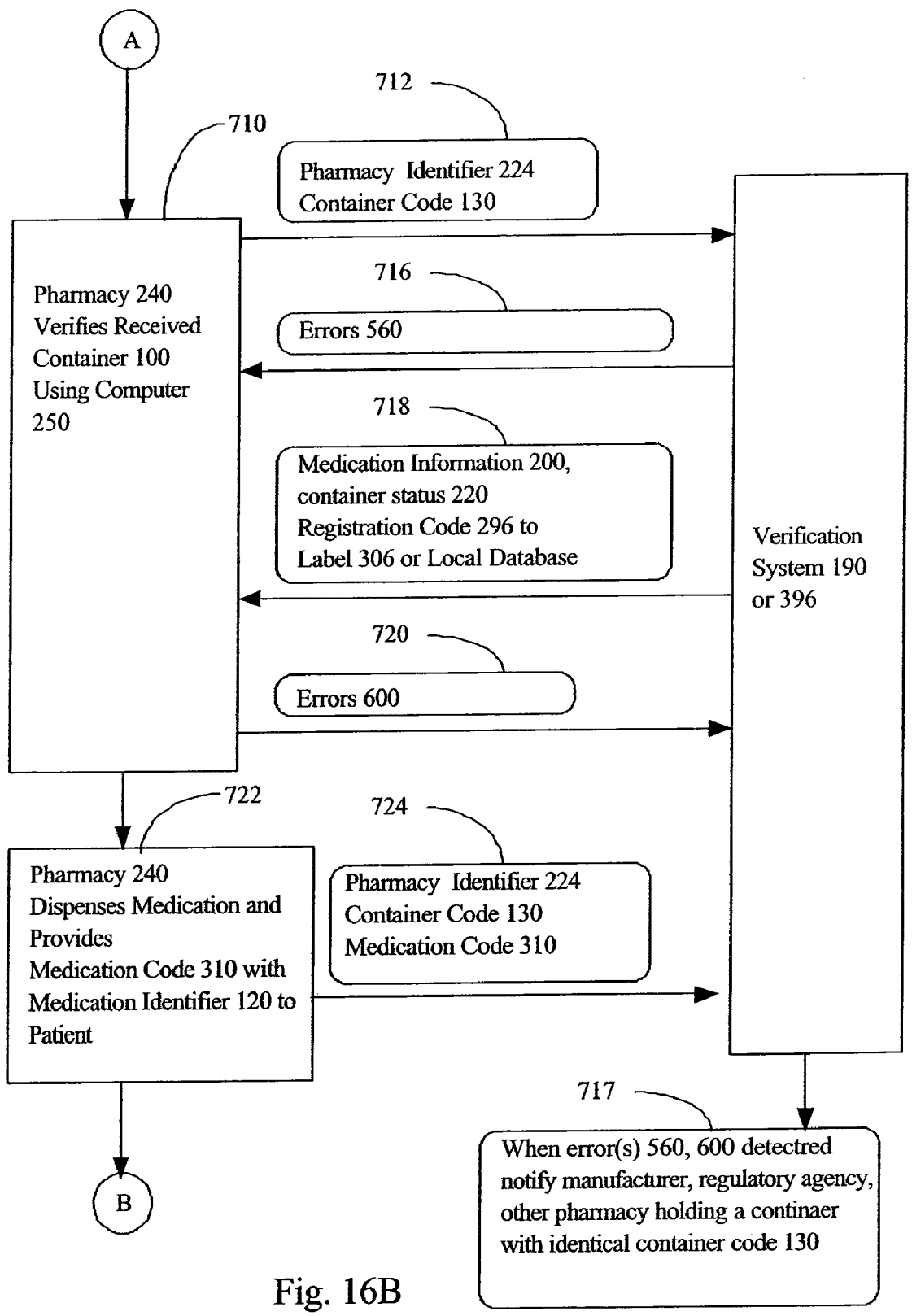
Figure 16C:
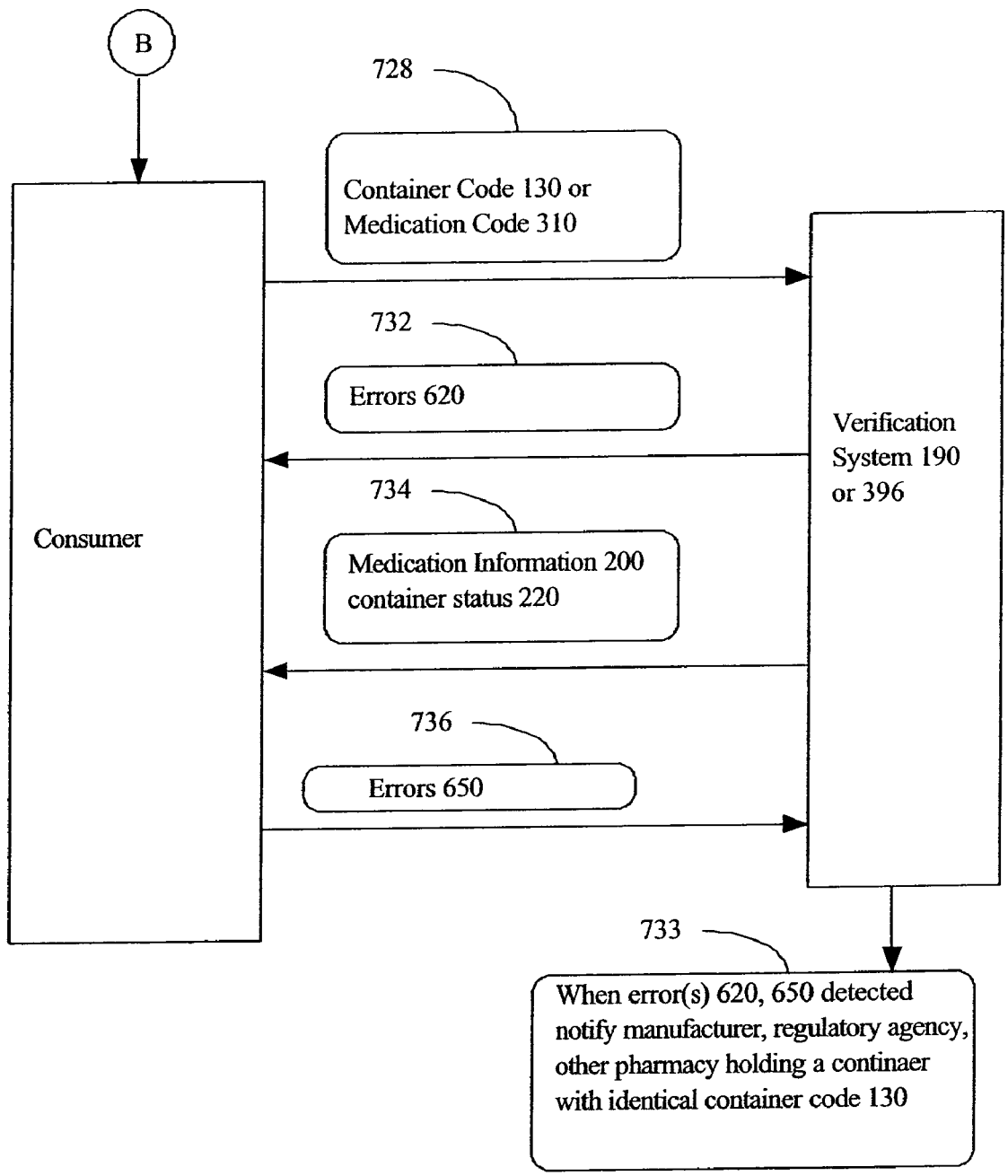

When medication 104 is packaged by a manufacturer 102 or repackager container code 130 is selected and printed on, attached to, or recorded to container 100 (Step 700, see FIGS. 16A, 16B, and 16C for related Steps). This process can be performed before or after container is filled and container code 130 can be obtained from a prerecorded set of labels or tags. Container code 130 and medication information 200 are entered into database 184 of verification system 190 (Step 701) after manufacturer 102 has properly identified themselves via a password, code, or key. Database 184 can be a single database or a collection of separate database that are linked together, shared, or in communication with each other. Portions of database 184 can be maintained by a centralized verification agency or one or more medication manufacturers 102.

When container 100 is shipped (Step 702) additional information about its shipping destination 222 is recorded as part of container status information 220 in database 184 (Step 703) and linked to container code 130 so that when code 130 is provided to verification system 190 status information 220 can be retrieved.

When container is received by pharmacy 240 (Step 710), container code 130 can be provided to (e.g. by keyboard) or scanned by (e.g. using transducer 260) computer 250 and sent to verification system 190 (Step 712). It is anticipated that pharmacy 240 will also send pharmacy identification 224 or pharmacy identification information 244 (see FIG. 6) to system 190 so that only pharmacies that are registered with verification system 190 are allowed to interact with it. System 190 can interrogate database 184 to determine if any error conditions exist, which if present will be returned to pharmacy 240 as part of errors 560 (see FIG. 12 and Step 716).

For example pharmacy identification 224 or pharmacy identification information 244 can be checked to determine that it has been entered in or registered with database 184 of verification system 190. If not verification system 190 can refuse to interact with further communication from pharmacy 240 (e.g. by blocking communication from the Internet address associated with the request. It is assumed that pharmacy identification information 244 are allocated in a unique, generally non-sequentially manner so that an arbitrary guess will only have a small chance of being correct. To further improve security, a report can be provided to each pharmacy of every medication code 130 verified in a day, week, or month, allowing the pharmacy to detect unusual or unauthorized verification attempts. This will alert pharmacy 240 in case some one else is using their identification information 244. In some cases verification system 190 can use simple rules or computer heuristics to detect if an abnormal number of verification requests are being presented or that the requests differ from those commonly requested by pharmacy 240. In either case verification system 190 can notify the pharmacy 240 staff or verification system 190 staff regarding the number or type of verification requests made.

Another example of an error is when the provided container code has not been entered into database 184, this is a clear indication of an error and likely fraudulent medication and error message 570 will be sent to pharmacy 240. In this case container code 130 may have been entered incorrectly (e.g. when code 130a is entered manually). Entering it correctly will remove the error condition. If the error condition persists an error notification may also be sent to the manufacturer 102 corresponding to container code 130, a regulatory agency, or other interested parties (Step 717).

When the pharmacy identifier 224 differs from the receiving ship destination 222 to which medication 104 was shipped (when this information is known) or the country of the pharmacy differs from the destination country error message 572 can be created. If container code 130 has been entered by another pharmacy 240 (e.g. the same code is entered by two different pharmacies), one of them likely has a fraudulent container 100 or one pharmacy sent container 100 to the other. In this case the message can be sent from the verification system 190 to both pharmacies indicating that the containers 100 with container code 130 should be quarantined for further explanation or examination. Should the pharmacies be able to document that one sent container 100 to the other pharmacy, then the verification system 240 will update its database to reflect this change.

When the above test pass, verification system 190 uses code 130 to retrieve a portion or all of medication information 200 and status 220 and transfer them to computer 250 (Step 718). The pharmacist uses information 200 and status 220 to determine if there is a possible error regarding container 100 and its contents. For example if the medication container 100 does not actually contain the medication 104 indicated by medication name 120 (e.g. label 118 indicated medication 104 corresponding to name 120 is in container 100 and it differs from medication name 120) pharmacy 240 can return error message 610 (see FIG. 13 and Step 720). Other checks are anticipated. When any of them fail container 100 can be quarantined by pharmacy 240 and additional parties can be notified of the error, e.g. regulatory agencies, the manufacturer 102, etc (Step 717).

Figure 8:
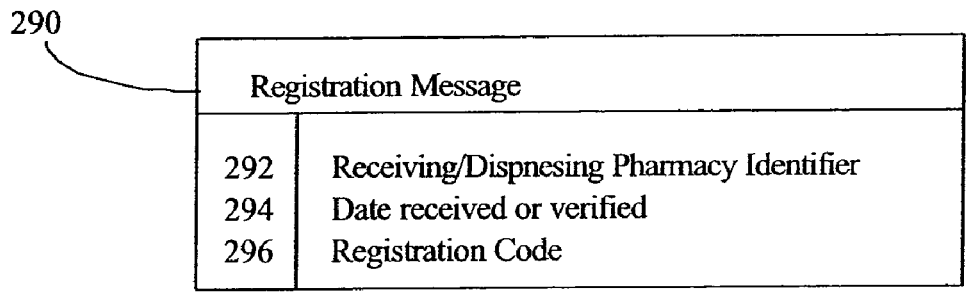
FIG. 8 is a registration message sent by verification system to a pharmacy.

When all the tests pass, verification system 240 can send a registration message 290 (see FIG. 8) to computer 250 which in turn writes the message via transponder 260 to tag 130c when tag is a read/write memory. Appropriate checks, such as read after write can be preformed to verify that message was written to tag 130c. Alternately or in duplicate, registration message 290 can be recorded in computer 250 or verification system 396 with container code 130 (e.g. when container code 130 is not written to tag 130c). Message 290 typically can include the receiving/dispensing pharmacy identifier 292, the date it was received or verified 294, when desired a unique registration code 296, and other useful information. Registration message 290 is used as described below.

III. Dispensing Medication 104 by Pharmacy 240

Pharmacy 240 after checking container code 130 with verification system 190 and determining there are no errors can use container 100 to dispense medication 104 for a patient. Pharmacy 240 can check container code 130 with verification system 190 as described above every time medication 104 is dispensed. However, when financial charges apply to verifying container code 130 or when it is more convenient, pharmacy 240 may check container code 130 only once, e.g. when received. After checking verification system 396 initially the pharmacy 240 can make an entry in computer system 250 or verification system 396 that container code 130 has been successfully verified. Thereafter, pharmacy 240 can instead check to determine that container code 130 is entered into computer 250 or verification system 396. If it is registration message 290 can be retrieved. When registration message 290 is recorded to RFID tag 130c, it can be read from tag 130c along with container code 130.

When mediation is dispensed for a patient in container 300 or 100 a prescription label 306 is prepared by printer 270 as previously described a receipt 320 can be printed by printer 270 or other (Step 722). Medication code 310 is then written to label 306, tag 310c (via transponder 260), or receipt 320 It is anticipated that medication code 310 is linked to container code 130 (Step 724) in verification system 190 or 396 and also linked to registration message 290 when it is available.

When a first container 100 is only able to fulfill a partial request for a quantity of medication 104 and second container 100' (a different by medication container than container 100) is used to obtain the remaining amount of medication 104, medication code 310 can be linked in verification system 396 to the continuer codes 130 for the first and second containers 100. In some cases label 306 or receipt 320 can have the container codes 130 from both the first and second containers printed on them or programmed to tag 310c. In this manner information about both the containers that were used to dispense medication 104 to container 300 can be verified by verification system 396.

IV. Operation of the Verification System 396 with Container 300

The patient using computer 450 can enter medication code 310 into a data retrieval (Step 728) program (e.g. an Internet browser) to contact verification system 396. Verification system 396 can determine the presence of several errors 620 (see FIG. 14) which can be sent to the patient. To add an additional layer of trustworthiness to this interaction, the patient may need to be registered with verification system 396 (e.g. via a password, unique cookie, or computer identifier of the patient's computer 450 or automated dispenser). In this manner verification system 396 is not provided with medication code 310 by untrustworthy Internet verification sessions.

Some errors may be caused by the patient incorrectly entering medication code 310, e.g. by mistyping, in which case the patient can be given the opportunity to reenter the code. The patient may be allowed to reenter medication code 310 a limited number of times (e.g. 3 times) after which verification system 396 can terminate interaction with this patient for a period of time (e.g. 8 hours). This is easiest to do when the patient has a relationship or is registered with verification system 396. However, if the patient continues to enter the same medication code several times it can be presumed that the patient is entering it correctly but that it is not in the database of verification system 396 an error message will be presented to the patient.

Some errors indicate the patient should not consume medication 104 for safety reasons (e.g. recall 636, expiration date 638, or new contraindications 228 errors). Other errors 630, 632, and 634 can indicate a problem with the medication dispensing or tracking process and that medication 104 may be fraudulent (step 732). Verification system 396 can indicate this to the patient, to the manufacturer 102, or to a regulator agency for additional review (Step 733). The patient may be instructed to return medication 104 and container 300 to the pharmacy or to contact the verification system 396 for additional precautions.

When there are no errors detected, verification system 396 will retrieve information related to or linked to medication code 310, e.g. container code 130, medication information 200, container status 220, registration message 290, and/or dispensed medication information 340 (Step 734). The patient can further compare medication information 200 with label 306 or receipt 320 and with the actual contents of container 300 or 100. When there is a mismatch the patient can send patient check error 650 (see FIG. 15) to pharmacy 240, verification system 396 (Step 736), to the manufacturer 102, a regulatory agency, or other responsible party. The patient is then prevented from being exposed to fraudulent medication 104. When pharmacy 240 determines a valid medication dispensing error has been detected can contact other patients to whom the same medication 104 corresponding to container code 130 has been dispensed.

The patient can also compare pharmacy and distribution information related to the container status 220. If the patient identifies that the pharmacy 240 that dispensed medication 104 to them does not correspond to receiving pharmacy identifier 292 or dispensing pharmacy 350 they can identify this error to verification system 396 or other interested parties. Similarly the patient can detect if ship destination 222 identifies a country or other location unlikely to dispense medication 104 to him.

It is assumed that even if only a few patients who receive medication 104 from pharmacy 240 retrieve information from verification system 396, that many other patients' will be protected by such checking. Furthermore all pharmacies using verification system 190 or 396 will likely be checked often enough to prevent them form dispensing any medication 104 not properly labeled and verified.

V. Inventory

When pharmacy 240 is going to discard container 100, a notice can be sent to verification system 190. This can be aided when verification system 190, pharmacy computer 250, or tag 130c maintains an inventory of how much medication 104 was originally in container 100 and how much has been dispensed. In this manner automatic determination can be made that container 100 is empty when the last portion of medication 104 in container 100 has been dispensed.

As described above this can be done by verification system 190 or pharmacy computer 250. In some cases tag 130c is used to maintain the inventory and checked by system 190 or computer 250 every time medication 104 is dispensed in other cases it is performed by a pharmacy employee when medication 104 is dispensed by this person and manually entered into system 190 or computer 250. When container 100 is determined to be empty container code 130 should be marked as no longer in use. When verification system 190 or pharmacy computer 250 is used to track the quantity of medication 104 dispensed by pharmacy 240 any attempt to print label 306 or receipt 320 (when printer 270 or transducer 260 is in part controlled by verification system 190) can be denied by verification system 190 when the quantity of medication 104 already dispensed exceeds the amount originally in container 100. This will prevent pharmacy 240 from attempting to use container code 130 to dispense medication 104 not related to container 100.

VI. Related Issues

It is anticipated that a medication manufacturer 102 can send container 100 first to a distributor and that the distributor can have a computer similar to computer 150 or 250. Distributor can read container code 130 and send this code with information identifying the distributor to verification system 190, which will enter or link this information to container code 130 for later retrieval (Step 703). In this manner every step of the distribution to dispensing chain of ownership can be documented and maintained and provided for review to the pharmacist and/or patient. Medication information 200 and container status 220 can be sent to the distributor for additional action, e.g. the medication 104 may be recalled in which case the distributor will quarantine container 100 and return it to the manufacturer 102.

When pharmacy 240 is to send container 100 to another pharmacy, a notification of this fact can be sent to verification system 190, so that when the next pharmacy receives container 100 and attempts to verify container code 130 no errors will be returned indicating that it is still thought to be at the first pharmacy.

VII. Application to Other Markets

As a convenience and to improve clarity items discussed below with a similar purpose to those described above will be referred to using identical numbers.

It is anticipated that other markets can benefit from similar verification processes where a product 104 is released or shipped to a company 240 or person with a product label 118 including a product identifier 120 (e.g. product name) and a unique, difficult to guess product code 130 that is linked to additional information 200 about the product and/or information about the status 220 of the product (e.g. shipping information, recall data, that it was previously purchased etc) stored in a verification system 190 database 184 (Steps 700, 701, 702, and 704). The company 240 or person receiving the product may be required to identify themselves using identification information 244 prior to accessing verification system 190 or 396 or process (Step 706 or 712) so that only parties who are members or registered with verification system 190 or with the manufacturer 102 are provided information.

Some errors indicating a fraudulent product can be automatically detected, e.g. an unregistered product code 130 is presented for verification or when a product code 130 is presented to the verification system 190 by two different companies 240, an error message 560 can be sent by the verification system 190 to both companies and to the original manufacturer 102 that the same product 104 has been reported by two different locations. Using this system, manufacturer 102 can be notified when improperly coded or fraudulent products 104 are detected and can take steps to ensure that they are not sold, used, or further distributed (Step 717).

Next the product code 130 is used to retrieve the product information 200 and/or status 220 for comparison by a company 240 or person that receives the product (Step 718) who can detect other errors, e.g. the product 104 received does not correspond to the retrieved product information 200 and 220. These errors can be reported by the company 240 receiving the product (Step 716) to the verification system 190, the original manufacturer 102 or public safety agency.

When the product 104 has a memory read/write tag 130c a registration code 296 can be prepared by the verification system 190 and written to the tag 130c for later use. Alternately, the registration code 296 can be recorded in a database, e.g. 184. In some cases product 104 can be limited so that it can not be used or dispensed if the registration code 296 is not present or if the product code 130 is not verified. This can further be extended to cover the instance where manufacturer 102 has not listed or does not recognized company 240 as being qualified to use product 104. This can be determined by verification system 190 checking company identifier 292 or identity information 244 of company 240 with manufacturer 102.

The product 104 can in turn be dispensed or redistributed and can bear the original product code 130 or can be relabeled (Step 722). The new labeling will include a product identifier 120 (e.g. name) and a different or second (preferably unique) verification code 310 that can be used to retrieve the original code 130, and/or product information 200, and/or product status 220, and/or dispending information. The company or person that in turn receives the dispensed container 300 can then use the verification code 310 to obtain the information above to determine if there is a problem and that the product is fraudulent or is not suitable for use or consumption.

When the verification code 310 is presented to the verification system 190 by two different companies or persons to whom the container 300 was dispensed an error message 620 can be sent to both companies or persons and to the original manufacturer 102 that the verification code 310 was used twice to label two different containers 300.

VIII. Ensuring Retail Purchases Using a Financial Verification Card 800 are for Genuine Products 104

As a convenience and to improve clarity items discussed below with a similar purpose to those described above will be referred to using identical numbers. However, when two similar items are discussed one will have an apostrophe appended to it to clarify the distinction between the two items.

Many retail and other purchases are conducted using a credit card, debit card, prepaid cash card, or other financial verification card 800. As shown in FIG. 17 these purchases are a guarantee between card holder or customer 802, card issuer 804 (e.g. bank), and retailer 240 that the retailer 240 will sell the product to card holder 802, card issuer 804 will pay retailer 240, and card holder 802 will reimburse the card issuer 804. In many cases card issuer 804 may also be insuring the card holder 802 against damages in case card 800 is stolen and fraudulently used. Some card issuers 804 also provide added warranty coverage or insurance for products 104 purchased with their cards and the card issuer 804 also protects the card holder 802 when faulty product 104 is to be returned to retailer 240 for a refund.

As shown in FIG. 18 card 800 typically has the card issuer's name 810, card holders name 812, account number 814, expiration date 816, and magnetic strip 818 (typically on the rear), and/or electronic chip 820. Cash cards may have less information, e.g. they many not have card holder's name 812 or expiration date 816. While card is shown as a physical element it may also be computer token or account number, a personally memorized financial account, or it can take the form of check. In this case card issuer 804 is a financial company that provides financial and other assurances between customers 802 and retailer 240

Purchases made with verification card 800 can be verified as described above. However, some extra steps can improve the system and provide additional protection card holder 802 as described below.

Figure 21:
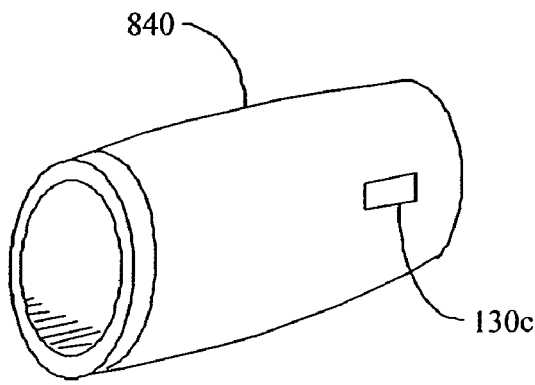
FIG. 21 is a perspective view of a product with a product code attached to it.

As before manufacturer 102 builds product 104 that is sent to retailer 240. Product 104 has product code 130, e.g. in the form of a RFID tag 130c, attached to it, strapped to it, linked to it, or is packaged in a container 100 that has product code 130; representative examples of this are shown in FIGS. 19 to 21. FIG. 19 shows product 104 as a purse 830 or bag with strap 832 that links purse 830 to manufacturer logo tag 834 with RFID tag 130c inside it. FIG. 20 shows watch 836 in container or box 100 with RFID tag 130c as part of box wall 838. Other examples include RFID tag 130c sewn into clothing, or connected by a plastic locking loop 832 as frequently use with apparel. Finally another example as shown in FIG. 21 is jet engine 840 with RFID tag 130c glued or riveted to it.

Product code 130 as before is a large unique, generally non-sequential number chosen in a manner to prevent easy guessing of even a single product code 130 over the production life of a product, e.g. a one in a million chance of being guessed although other probability levels can be used that provide a reasonable assurance a valid product code 130 will not be guessed.

However, when product code 130 is in the form of tag 130c, the tag can be equipped with encryption capabilities so that only a reader (or writer when it is read-write) presenting the correct code numbers or key can read the content of tag 130c or the product code 130 is encrypted before being read by compatible reader or transducer 260 that is capable of decrypting it. In this situation the product code may be sequential, but the encryption techniques prevent unauthorized parities from reading the tag 130c to discover product code 130 or to create and write a fraudulent product code 130 to tag 130c.

Manufacturer 102 provides their identity to verification system 190 in the form of a password, cookie, virtual private network exchange, identification number, or key. Verification system 190 determines that manufacturer 102 is registered in database 184; if they are not further communication is terminated. This prevents product code 130 from being entered by a fraudulent group posing as a manufacturer.

When manufacturer 102 is registered product code 130 is sent to verification system 190 and is entered into database 184 with product information 200 so that by providing product code 130 product information 200 can be retrieved. Product information 200 can include product name 120, product manufacturer information 211 (e.g. name, identifier, and contact information), product size/concentration 212, form/shape 214, manufacturing lot or serial number 216, expiration date 218, and other data relevant to product 104 at the time of manufacturing. Manufacturer 102 can be charged a fee by verification system 190 for each product registered so that verification system 190 will store product code 130 and related information for future verification purposes.

Information 200 can also be accessed by product code 130, or in some cases by product name 120, and/or lot number 216. Similarly, code 130, name 120, or lot number 216 can be used to add information about a product to server 182 or database 184. When or after product 104 with or without container 100 is shipped to a distributor or retailer 240 additional information can be stored in database 184 or linked to database and is referred to as product status information 220 (see FIG. 5). Status 220 can include the destination 222 to which product 104 was shipped, the retailer 224 that received product 104, the recall status 226 of the product 104, product code error flag 229 (e.g. product code 130 was reported received by another retailer or other error states), and any other information about the product, e.g. when product 104 is sold account number 814 or card holders name 812 of the customer 802 that purchased product. When a product is recalled, recall status 226 can be updated by providing only product name 120 and/or lot number 216 to server 182 or database 184.

Database 184 is either accessible, run by, and/or owned by a financial verification company or card issuer 804 that provided card 800 to its card holder 802.

When product code 130 is already printed (e.g. preprogrammed RFID tags) and then applied to product 104 or pre-applied to product 104 (e.g. by the product manufacturer 102), computer 150 can use transducer 160 to read code 130 (text, bar code or RFID tag) and enter it into database 184 along with product information 200. Alternately, when product code 130 is text it can be manually entered using keyboard 156.

Figure 7:
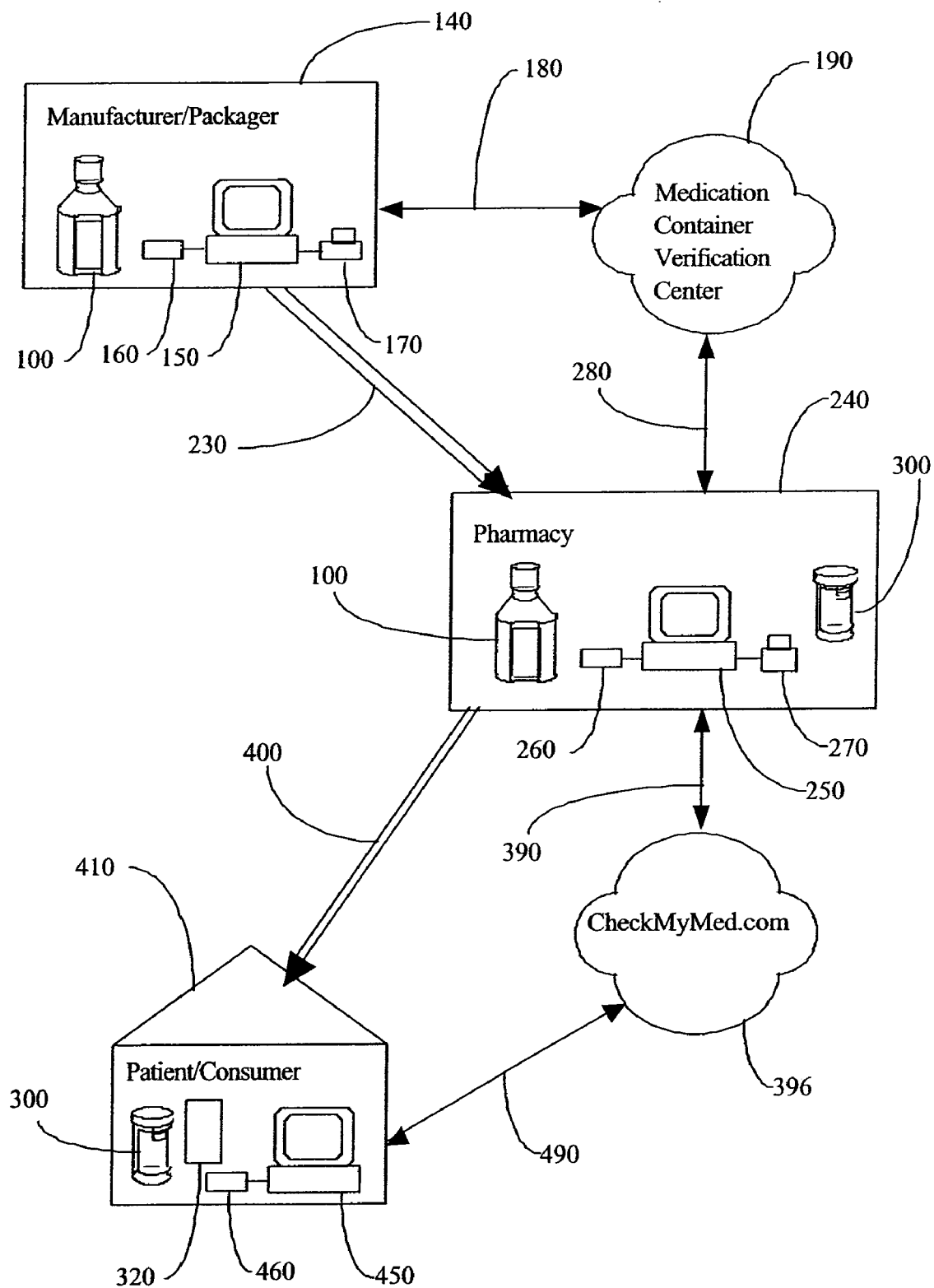
FIG. 7 is a schematic view of medication containers and related information that are tracked and verified from manufacturer to pharmacy and from pharmacy to patient.

Referring to FIG. 7, when product 104 has been built and labeled with product code 130 or placed in container 100 with product code 130, it enters transportation system 230 and is received by retailer 240. Retailer 240 has a computer 250, which is for purposes of discussion a similarly equipped as computer 150. Computer 250 is linked to transducer 260, which can be used to read product code 130 (text, bar code, RIFD tag) related to product 104. When product code 130 is text it may be entered manually using a keyboard attached to computer 250. For most retail products additional labeling is not prepared for product 104. Computer 250 uses communication network 280 to interact with verification system 190 and database 184.

When product 104 is received by retailer 240 product code is read with reader 260. The computer 250 (or reader 260 when so equipped) transmits retailer identifier 244 (which may include a password or encryption key) to verification system 190. Verification system 190 checks that retailer 240 is registered. If the retailer 240 is not registered no further communication conducted by verification system 190. When retailer 240 is registered verification system 190 receives product code 130 and checks to determine that it is in database 184. If not an error message is sent to retailer 240.

To prevent a dishonest retailer 240 from attempting to guess a registered product code 130, verification system 190 may limit the number of times retailer 240 can enter in product codes 130 that are not registered in verification system 190. This is primarily a concern when product code 130 is manually entered and mistakes can happen. Retailer 240 may be asked to reenter product code 130 a few times (e.g. a limit of 3 times) and then be blocked from further entries for a period of time (4 hours). A retailer 240 with a pattern of presenting product codes 130 that are not registered may be investigated by verification system 190 and/or manufacturer 102. Product codes read by a bar code or RFID tag reader 260 should not have any transcription errors or only a much lower level of errors tolerated.

If product code 130 is in database 184 a further check is performed to determine if product status 220 related to product 240 indicates that product 104 has been previously sold to a previous customer 802' as stored in product status information 220. When it has been reported as previously sold the retailer 240 is asked to place product 104 in quarantine and to not sell it. Verification system 190 can send an investigator to review the authenticity of product 104 and product code 130 or ask to have product 104 sent to it or manufacturer 102 for further investigation.

When verification system 190 has knowledge of the customer 802' who previously purchased a product 104 (e.g. stored in product status 220) with the same product code 130 a message is sent to customer 802' (e.g. by e-mail or letter) indicating to them that product 104' they purchased on a previous date may be fraudulent. The verification system 190 can instruct customer 802' to return previously purchased product 104' and its product code 130' to the retailer 240' from whom they purchased product 104' or to an accepted return agency in the case the original retailer 240' is far away or no longer in business so that the validity of product 104' and its product code 130' can be determined. Purchase receipt 320 for product 104 may also be request to be presented to retailer 240. If either is determined to be fraudulent a replacement product 104 can be given to customer 802' or he can be given a refund of the purchase price.

If product 104 has not previously been sold, product information 200 and product status 220 can be sent to retailer 240 who in turns determines that product 104 corresponds to information 200 and that status 220 is in accord with the retailer expectations (e.g. that product 104 wasn't for foreign shipment or that it is of recent manufacture, etc.). If not the retailer 240 should notify verification system 190 of the discrepancy and quarantine product 104 for later examination of it and product code 130 or return it to manufacturer 102.

Provided there are no errors retailer 240 can place product 104 in stock or sell it. In many cases retailer 240 may only check product code 130 with verification system 190 when customer 802 has selected it for purchase.

When product 104 is being purchased product code 130 is read by reader 260 and customer 802 provides their financial verification card 800 which can also be read by reader 260 or another reader if needed. Retailer 240 transmits retailer identification 244, product code 130 and customer name 812 and account number 814 to verification system 190. Verification system 190 performs the above mentioned checks to determine that product 104 can be sold and that account number 814 corresponds to a financial account that is approved for this purchase. Product information 200 and product status 220 are sent to retailer 240 to verify that product 104 corresponds to the one described by product information 200 and product status 220. Any errors are treated as described above.

Figure 22:
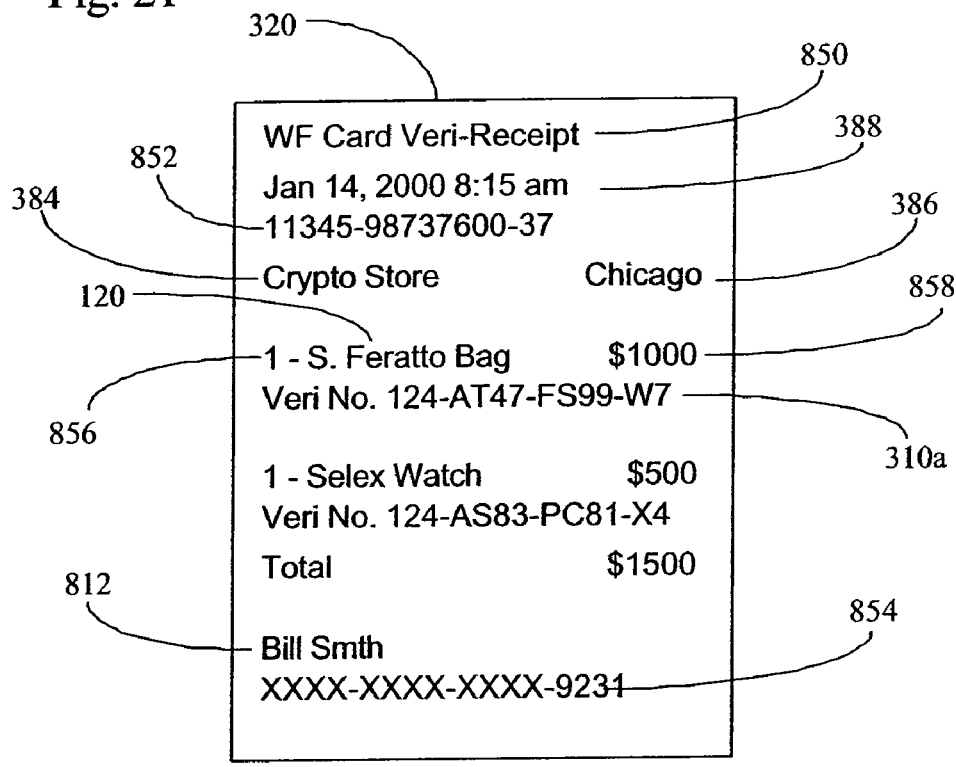
FIG. 22 is another sample of a receipt related to a financial transaction using a verification system to verify a product is genuine.

When no errors are present verification system 190 registers the card holder (e.g. name 812 or account number 814) in product status 220 for product 104. Typically, retailer 240 and/or card issuer 804 prepares one or more receipts or credit card slips 320 (see FIGS. 22 and 11) printed by printer 270 for customer 802 to take and often to be signed. Receipt 320 typically includes the name 850 of the verification system 190 (which may be the same as card issuer 804), the date and time of the transaction 388, the retailer name 384, the retailer location 386, transaction number 852 that identifies the purchase transaction (which may also be a large number selected in a unique generally non-sequential manner), customer name 812 and frequently a portion of their card account number 854. It is anticipated that receipt 320 can also be in the form of an electronic receipt and is not printed, but instead provided to customer electronically for storage in an electronic wallet or PDA (personal digital assistant) or cell phone.

Also on receipt 320 for each product 104 purchased is printed a portion of product description or information 200 (e.g. product name 120, size, or quantity per unit), number of units purchased 856, price 858, and verification code 310 are listed. Verification code 310 is a unique generally non-sequential code that has a low probability or being guessed, e.g. less than on in a million over the life of the verification system 190. Other probabilities can be selected to make it difficult to arbitrarily guess verification code 310. Verification code 310 can be the same as product code 130 when it is printed as alphanumeric code 130*a* or bar code 130*b*, but generally it is not the same when RFID tag 130*c* is used so that product code 130 remains a secret. However, by making verification code 310 different from product code 130 it makes it prevents someone who reads product code 130 to interact with verification system 190.

Verification code is linked in verification system 190 to product code 130. A separate verification code 310 can be printed when multiple units of product 104 are purchased at one time. In some cases transaction number 852 is recorded in verification system 190 and links all the products 104 on a single receipt 320 to the individual product codes 130. Additional partial receipts can be printed by retailer 240, e.g. a gift receipt, where only a portion of the products 104 are listed and typically no prices are printed. However, these additional receipts can still have verification code 310 printed for each product 104.

Verification system 190 can charge retailer 240 or customer 802 a verification charge for verifying that product 104 is not fraudulent. Verification system 190 will then guarantee that product 104 is genuine and if there is a concern in the future as to whether it is genuine verification system can re-verify it and any time a product is found not to be genuine verification system 190 will reimburse customer 802 and/or retailer 240 for the purchase price 858.

After purchase customer 802 transports 400 product 104 and receipt 320 to the customer's home 410 or to any other site where he has access to a computer 450. Computer 450 is configured similarly to computer 150 or 250 with a processor, memory, display, keyboard or pointing device (not all shown). Computer 450 can be linked to a transducer 460 which can read text, bar codes, RFID tags or other information sources and is similar to transducers 160 and 260. Computer 450 can communicate via network 490 (e.g. the Internet) with verification system 190.

To add an additional layer of trustworthiness, customer 802 may need to be registered with verification system 190 (e.g. via the account number 814, a password, unique cookie, or computer identifier of computer 450). In this manner verification system 190 is not provided with verification code 310 by untrustworthy Internet verification sessions.

Customer 802 using computer 450 enters verification code 310 into a data retrieval (Step 728) program (e.g. an Internet browser) to contact verification system 190. Verification system 190 can determine the presence of several errors 620 which can be sent to customer 802. Note that error 630 related to a bad verification code 310 can be caused by customer 802 incorrectly entering verification code 310, e.g. by mistyping, in which case the patient can be given the opportunity to reenter code 310. However, customer 802 must exercise some diligence in entering verification code 310 as verification system 190 may attempt to limit the number of retries customer 802 can reenter verification code 310. This is done to prevent customer 802 from attempting to randomly guess a valid verification number 310 possibly for fraudulent purposes. When verification system 190 determines that customer has exceed a limit in the number of retries customer 802 can be blocked from making further entries (e.g. for 8 hours).

When customer 802 has properly entered verification code 310 errors 630, 632, and 634 can be reported indicating a problem with the selling or tracking process and that the product may be fraudulent (step 732). Verification system 190 can indicate this to the customer 802, to manufacturer 102 (Step 733). Customer 802 may be instructed to return product 104 and corresponding product code 130 to the retailer 240 for a replacement product 104 or refund when product 104 is determined to be fraudulent or to contact verification system 1900 for additional precautions.

Verification system 190 can determine that product code 130 associated with verification code 310 (when not the same code) was previously used in a transaction with a different customer 802', error 860. When this is the case verification system 190 notifies customer 802 and instructs them to return product 104 as discussed above. Verification system 190 can also contact the different customer 802' to return their product 104' and product code 130' for a refund or replacement should product 104' they purchased be fraudulent. Purchase receipt 320 may also be requested for presentation to retailer 240. This service can be part of a guarantee verification system 190 provides to customers 802 and retailers 240 that use its system.

When there are no errors detected, verification system 190 will retrieve information related to or linked to verification code 310, e.g. product code 130, product information 200, product status 220, and registration message 290. Customer 802 can further compare product information 200 with product 104 or receipt 320. When there is a mismatch the customer can send customer check error 650 to retailer 240, verification system 190 (Step 736), to manufacturer 102, or other responsible party. The customer can return product 104 with product code 130 and receipt 320 for a refund to replacement.

Customer 802 can enter verification number at a later date, e.g. when the product is being resold several years later, as a means of proving to a purchaser that it is genuine. Any other errors discussed above can be reported and product information 200 and product status 220 can be retrieved. However, customer 802 may be charged a fee of this verification service after a time period has passed (e.g. 1 month) from the original purchase or based on the number of times customer 802 has used verification system 190 to verify verification number 310 (e.g. more than 2 times). Verification system 190 can also allow customer 802 to indicate that product 104 has been sold to a new person and therefore have product status information 220 updated. Additional charges by verification system 190 may also apply to this activity.

Customer 802 may decide after making a purchase of product 104 to return it for a refund or exchange it for another product 104. When this happens customer 802 brings back product 104, the original boxes 100 (or other packing), product code 130, and receipt 320. Retailer 240 reads product code 130 from product 104 or container 100, notifies verification system 190 of the retailers identity 244 and provide transaction number 854 and verification code 310 and specify that product code 130 is not longer to be associated with customer 802 but instead should be listed as in the stock of retailer 240 and that customer 802 should be credited with the amount of purchase price 858. Should verification system 190 determine that there is an error, for example verification code 310 is not linked to product code 130 or transaction number 854 is not related to product 104 the return of product 104 can be terminated, or product information 200 or product status 220 is not related or doesn't match product 104 being returned. This prevents someone form returning a fraudulent product as though it was an original product.

When a product 104 is returned by retailer 240 to the manufacturer 102, e.g. as part of a recall or inventory adjustment, retailer 240 can read product code 130 from product 104 and indicate to verification system 190 that product 104 is being sent back to manufacturer 102. Alternately, manufacturer 102 may read product code 130 when product 104 is received for return or restocking and send a message to verification system 190 that product 104 is not longer in distribution or sale.

A similar process is performed when one retailer 240 has verified a product 104 in stock and subsequently exchanges or sells it to another retailer 240', e.g. when adjusting inventory levels. This way product 104 is now listed as with retailer 240'. However, it should be noted that some products 104 can be restricted by manufacturer 102 as to which retailers 240' can sell it. In this case any time verification system 190 is presented with a product code 130, retailer identity 384' can be sent to manufacturer 102 to check to determine if that retailer 240' is qualified or allowed to sell it. If they are not the verification system 190 will notify retailer 240' of this and verification system will not provide a verification code 310 for product 104. This will present notice to customer 802 that product 104 is either fraudulent or being purchased from retailer 240' that is not cooperating with verification system 190 or not allowed by manufacturer 102 to sell product 104. Verification system 190 will not guarantee product 104 and either no receipt 320 will be printed or verification code 310 will not be printed or a special message can be printed on receipt 320 that verification of product code 130 was not allowed or performed While some embodiments of verification card 800 have been described as a credit card and verification system 190 as run by a credit card company it may be desirable that verification card not be a credit card and verification system is run by a company or agency that has a relationship with customer 802, retailer 240, or manufacturer 140. As before verification system 190 provides a guarantee that product 104 purchased by customer 802 is authentic. For example verification system 190 can be run by an insurance company and card 800 can be issued by them or can be a credit card issued by a third party bank that can be used for this purpose as well. Receipt 320 can be the same as the receipt retailer 240 provides for purchasing product 104, but it can also be a separate transaction receipt used to authenticate product 104 as described above.

XI. Verifying and Tracking Products

Figure 23:
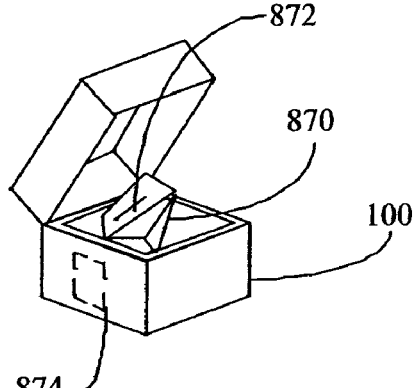
FIG. 23 is a perspective view of a raw material in a container with a material code.

In many cases there is concern over the origin, status, quantity, or quality of raw materials 870 (see FIG. 23) used to make product 104. This is especially of concern where the material 870 is expensive or some of the manufacturers or raw material 870 are subject to trade restrictions. For example, the frequently are concerns over the source of diamonds 870 used to make jewelry. Some diamonds 870 mined in specific countries are considered "blood diamonds" and some customers would prefer not to purchase jewelry using such diamonds 870. Customer 802 however, has no method of telling if diamonds 870 used in jewelry may be from a country of concern. This is even more of a problem when a piece of jewelry may consist of many diamonds 870 from several sources.

Verification system 190 can be used to reduce the problems associated with raw materials 870. When raw material 870 or product 104 is produced it is labeled 872, e.g. with diamonds a laser certification number can be etched in its surface. Raw material 870 is also placed in container 100, e.g. a box, sack, barrel, paper envelope or other packaging that is labeled with material code 874, e.g. a RFID tag or bar code. Material code 874 is similar in selection for product code 130, that is it is a unique generally non-sequential code that is not easily guessed. The producer contacts verification system and provides their identity (e.g. a password, virtual private network link, code number, etc.). Verification system 190 determines that the producer is registered. Other methods include applying bar codes or RFID tags with certification number. When the producer is registered with verification system 190 certification number 872 and material code 874 are entered into database 184 along with description of raw material 870 (e.g. mining company, country or origin, weight quantity, or quality) and other information related to raw material 870.

Raw material 870 is shipped to a material consumer, e.g. manufacturer 102. When raw material 870 is to be used manufacturer 102 provides their identity as a password, number or other distinctive means of identifying themselves in a trusted manner to verification system 190. Verification system 190 determines manufacturer 102 is registered or recognized, when they are recognized material code 874 is read by reader or transducer 160 and sent to verification system 190 with the amount of product 104 to be used which will be deducted from the stored quantity of raw material 870 to maintain an inventory level as discussed below. Label 972 can also be read (e.g. by eye or with a microscope), its contents entered (e.g. by typing) and sent to verification system 190. Verification system 190 then determines if material code 874 has been registered and if it matches label 872. If there is an error, verification system 190 returns an error message which will also occur if material code 874 is associated with a raw material 870 previously reported as completely consumed.

When there are no errors the amount of raw material 870 that is being used by manufacturer 102 is deducted from the amount previously entered. Manufacturer 102 can also identify a product 104 being made with raw material 870 and associate a product code 130 with product 104. Product code 130 is entered in database 184 or a different one and material code 874 or other related information about raw material 870 is entered in product information 200. In this manner a complete product may have multiple material codes 874 where each code is associated with a separate raw material 870 used to build it. It is now very easy for a customer 802 or retailer 240 to use product code 130 to retrieve product information 220 including all material codes 747 related to raw materials 870 and then retrieve the description for raw material 870 to determine the source of each raw material 870 used to build or process product 104 and that it was manufactured according to agreed upon specifications.

To apprise the public of the scope of this invention I make the following claims:

1. A method to verify a product produced by a manufacturer, the method comprising the steps of:
   a) attaching a unique product code to a product prior to delivery to a retailer;
   b) storing the product code with product information in a first database linked to a verification system associated with the manufacturer;
   c) distributing the product to the retailer; and
   d) selling the product from the retailer to a customer, the step of selling including the steps of:
      i. using a first computer to obtain the unique product code from the product;
      ii. providing the obtained product code to the verification system;
      iii. comparing the obtained product code with the stored product code; and
      iv. when the obtained product code and the stored product code match, preparing a receipt including a verification code and providing the receipt to the customer wherein the verification code is different than the obtained product code and wherein the verification code is used subsequently to identify at least one of the product code, product information, product status and product dispensing information.

2. The method of claim 1 further including the steps of obtaining customer information and storing at least one of customer information and the verification code in a second database linked to the verification system so that at least one of the customer information and the verification code is used to obtain the stored product code.

3. The method of claim 2 further including the steps of the customer using a second computer to submit the product code and at least one of customer information and the verification code to the verification system, determining by the verification system that the product code is associated with the submitted at least one of the customer information and the verification code and providing at least a subset of the stored product information via the second computer.

4. The method of claim 2 wherein the first and second database are a single database.

5. The method of claim 3 further including the steps of determining that the product code is not associated with the submitted at least one of the customer information and the verification code and providing an alert.

6. The method of claim 3 where the step of preparing a receipt includes the step of providing a portion of customer information on the receipt where the remainder of the information is known by the customer and the step of using a second computer to submit the product code and at least one of the customer information and the verification code to the verification system consists of providing at least the verification code and the remainder of the information known to the costumer and the verification system using the remainder of the information to determine that the customer is registered.

7. The method of claim 1 further including the steps of obtaining and storing customer information, determining the obtained product code corresponds to an invalid product where an invalid product is at least one of a recalled product, a counterfeit product, a product with a possibly duplicated product code and an expired product and, when the product is an invalid product, using the stored customer information to provide an alert to the customer.

8. The method of claim 7 further including the step of using the obtained product code to determine that the product is counterfeit and when the product is a counterfeit product, repaying the customer for the paid selling price.

9. The method of claim 1 wherein the step of providing the receipt consists of printing the receipt information on a label and attaching the label to the product.

10. The method of claim 1 wherein the step of attaching the product code to a product comprises attaching the product code to a container of medication.

11. The method of claim 1 wherein the step of attaching a unique product code to a product further includes the step of using an electronic memory to store the product code and attaching the electronic memory to the product.

12. The method of claim 1 wherein the step of attaching the unique product code to the product further includes at least one of writing the unique product code on a label and attaching the label to the product and transmitting the unique product code to a device that is physically associated with the product and storing the unique product code in the device.

13. The method of claim 1 further including the step of storing a list of authorized retailers in the database, the step of selling further including using the first computer to identify the retailer that is selling the product to the customer, indicating the identified retailer to the verification system, comparing the identified retailer to the authorized retailer list and performing a function as a result of the comparison of the identified retailer and the retailer list.

14. The method of claim 13 further including the step of storing a list of authorized products for at least one of the list authorized retailers in the database, the step of selling further including comparing the product code with the list of authorized products, and performing a second function as a result of the comparison of the product code and the list of authorized products.

15. The method of claim 1 further including the steps of the customer using a second computer to submit the verification code to the verification system, and the verification system using the verification code to identify at least one of the product code, product information, product status and product dispensing information.

16. A method to verify a product produced by a manufacturer, the method comprising the steps of:
   a) attaching a unique product code to a product prior to delivery to a retailer;
   b) storing the unique product code with product information in a first database linked to a verification system associated with the manufacturer;
   c) distributing the product to a retailer; and
   d) selling a portion of the product from the retailer to a customer wherein the portion is less than the entire product, the step of selling including the steps of:
      i. using a first computer to obtain the unique product code from the product;
      ii. providing the obtained product code to the verification system;
      iii. comparing the obtained product code with the stored product code; and
      iv. when the obtained product code and the stored product code match, preparing a receipt including a verification code and providing the receipt to the customer wherein the verification code is different than the obtained product code and wherein the verification code is used subsequently to identify at least one of the product code, product information, product status and product dispensing information.

17. The method of claim 16 further including the steps of obtaining customer information and storing at least one of customer information and the verification code in a second database linked to the verification system so that at least one of the customer information and the verification code is used to obtain the stored product code.

18. The method of claim 17 further includes the steps of the customer using a second computer to submit the product code and at least one of customer information and the verification code to the verification system, determining by the verification system that the product code is associated with the submitted at least one of the customer information and the verification code and providing at least a subset of the stored product information via the second computer.

19. The method of claim 17 wherein the first and second database are a single database.

20. The method of claim 18 further including the steps of determining that the product code is not associated with the submitted at least one of the customer information and the verification code and providing an alert.

21. The method of claim 16 further including the steps of obtaining and storing customer information, determining the obtained product code corresponds to the invalid product where an invalid product is at least one of a recalled product, a counterfeit product, a product with a possibly duplicated product code and an expired product and, when the product is the invalid product, using the stored customer information to provide an alert to the customer.

22. The method of claim 21 further including the step of using the obtained product code to determine that the product is counterfeit and when the product is a counterfeit product, repaying the customer for the paid selling price.

23. The method of claim 16 wherein the step of providing the receipt consists of printing the receipt information on a label and attaching the label to the product.

24. The method of claim 16 wherein the step of attaching the unique product code to the product comprises attaching the unique product code to a container of medication.

25. The method of claim 24 further including the step of determining that the quantity of all portions of the medication sold exceeds the total quantity of medication provided by the manufacturer as stored in the product information and providing an alert that the total quantity has already been sold.

26. The method of claim 16 wherein the step of attaching the unique product code to the product further includes the step of using an electronic memory to store the product code and attaching the electronic memory to the product.

27. The method of claim 16 wherein the step of attaching the unique product code to the product further includes at least one of writing the unique product code on a label and attaching the label to the product and transmitting the unique product code to a device that is physically associated with the product and storing the unique product code in the device.

28. The method of claim 16 further including the step of storing a list of authorized retailers in the first database, the step of selling further including using the first computer to identify the retailer that is selling the product to the customer, indicating the identified retailer to the verification system, comparing the identified retailer to the authorized retailer list and performing a function as a result of the comparison of the identified retailer and the retailer list.

29. The method of claim 16 wherein the step of selling a portion includes selling at least two portions and wherein the step of selling further includes, for each portion sold, performing steps (i) through (iv) where a different verification code is assigned to each portion sold.

30. The method of claim 16 further including the steps of the customer using a second computer to submit the verification code to the verification system, and the verification system using the verification code to identify at least one of the product code, product information, product status and product dispensing information.

31. A method to verify a product produced by a manufacturer, the method comprising the steps of:
  a) attaching a unique product code to a product prior to delivery to a retailer;
  b) storing the product code with product information in a first database linked to a verification system associated with the manufacturer;
  c) distributing the product to the retailer; and
  d) selling the product from the retailer to a customer, the step of selling including the steps of:
    i. using a first computer to obtain the unique product code from the product;
    ii. providing the obtained product code to the verification system;
    iii. comparing the obtained product code with the stored product code;
    v. when the obtained product code and the stored product code match, preparing a receipt including a verification code and providing the receipt to the customer wherein the verification code is different than the obtained product code; and
  storing a list of authorized retailers in the database, the step of selling further including using the first computer to identify the retailer that is selling the product to the customer, indicating the identified retailer to the verification system, comparing the identified retailer to the authorized retailer list and performing a function as a result of the comparison of the identified retailer and the retailer list.

32. A method to verify a product produced by a manufacturer, the method comprising the steps of:
  a) attaching the unique product code to a container of medication prior to delivery to a retailer;
  b) storing the unique product code with product information in a first database linked to a verification system associated with the manufacturer;
  c) distributing the product to a retailer; and
  d) selling a portion of the product from the retailer to a customer wherein the portion is less than the entire product, the step of selling including the steps of:
    i. using a first computer to obtain the unique product code from the product;
    ii. providing the obtained product code to the verification system;
    iii. comparing the obtained product code with the stored product code;
    iv. when the obtained product code and the stored product code match, preparing a receipt including a verification code and providing the receipt to the customer; and
  determining that the quantity of all portions of the medication sold exceeds the total quantity of medication provided by the manufacturer as stored in the product information and providing an alert that the total quantity has already been sold.

33. A method to verify a product produced by a manufacturer, the method comprising the steps of:
  a) attaching a unique product code to a product prior to delivery to a retailer;

b) storing the unique product code with product information in a first database linked to a verification system associated with the manufacturer;
c) distributing the product to a retailer; and
d) selling a portion of the product from the retailer to a customer wherein the portion is less than the entire product, the step of selling including the steps of:
   i. using a first computer to obtain the unique product code from the product;
   ii. providing the obtained product code to the verification system;
   iii. comparing the obtained product code with the stored product code;
   iv. when the obtained product code and the stored product code match, preparing a receipt including a verification code and providing the receipt to the customer; and
storing a list of authorized retailers in the first database, the step of selling further including using the first computer to identify the retailer that is selling the product to the customer, indicating the identified retailer to the verification system, comparing the identified retailer to the authorized retailer list and performing a function as a result of the comparison of the identified retailer and the retailer list.

34. A method to verify a product produced by a manufacturer, the method comprising the steps of:
   a) associating a unique product code to a first product prior to delivery to a retailer;
   b) associating a second unique product code to a second product prior to delivery to the retailer;
   c) storing the first and second unique product codes with first and second product information, respectively, in a first database linked to a verification system;
   c) distributing the first and second products to the retailer; and
   d) selling portions of the first and second products from the retailer to a customer, the step of selling including the steps of:
      i. using a first computer to obtain the first and second unique product codes;
      ii. providing the obtained product codes to the verification system;
      iii. comparing the obtained product codes with the stored product codes; and
      iv. when the obtained first product code and the stored first product code match and the obtained second product code and the stored second product code match, preparing a receipt including a single verification code and providing the receipt to the customer.

35. The method of claim 34 wherein the first product code is a first container code and the first product is a first medication in a first container and the second product code is a second container code and the second product is a second medication stored in a second container and wherein the verification code is a medication code.

36. The method of claim 35 further including the step of correlating and storing the medication code in a database with the first and second container codes.

37. The method of claim 35 wherein the step of selling further includes the step of placing portions of the first and second medications in a third container and presenting the third container to the customer.

38. The method of claim 36 further including the steps of, via a second computer, obtaining the medication code from the receipt, providing the medication code to the verification system, at the verification system and comparing the obtained medication code to the stored medication code.

* * * * *